(12) United States Patent
Ghosh

(10) Patent No.: US 7,109,235 B2
(45) Date of Patent: Sep. 19, 2006

(54) MICROTUBULE STABILIZING COMPOUNDS

(75) Inventor: Arun K. Ghosh, River Forest, IL (US)

(73) Assignee: The Board of Trustees of the University Illinois, Urbana, IL (US)

( * ) Notice: Subject to any disclaimer, the term of this patent is extended or adjusted under 35 U.S.C. 154(b) by 245 days.

(21) Appl. No.: 10/382,261

(22) Filed: Mar. 5, 2003

(65) Prior Publication Data

US 2003/0203929 A1 Oct. 30, 2003

Related U.S. Application Data

(60) Provisional application No. 60/362,499, filed on Mar. 7, 2002.

(51) Int. Cl.
*A81P 35/00* (2006.01)
(52) U.S. Cl. ...................................... 514/450; 549/270
(58) Field of Classification Search ................ 549/270; 514/450
See application file for complete search history.

(56) References Cited

FOREIGN PATENT DOCUMENTS

| EP | 1 295 886 | 3/2003 |
|----|-----------|--------|
| WO | WO 01/54689 | 8/2001 |
| WO | WO 02/064589 | 8/2002 |

OTHER PUBLICATIONS

Mulzer et al. (Angewandte Chemie, International Edition (2001), 40(20), 3842-3846.*
D.E. Pryor et al., *Biochemistry*, 41, 9109-9115 (2002).
A.K. Ghosh et al., *J. Org. Chem.*, 66, 8973-8982 (2001).
A.K. Ghosh et al., *J. Am. Chem. Soc.*, 122, 11027-11028 (2000).
A.K. Ghosh et al., *Tetrahedron Letters*, 42, 3399-3401 (2001).

* cited by examiner

*Primary Examiner*—Bruck Kifle
(74) *Attorney, Agent, or Firm*—Marshall, Gerstein & Borun LLP

(57) ABSTRACT

Laulimalide and epothilone derivatives useful as microtubule stabilizing agents, and in the treatment of cancers are disclosed. Methods of making the compounds and using the compounds as therapeutic agents in treating cancers also are disclosed.

6 Claims, No Drawings

MICROTUBULE STABILIZING COMPOUNDS

CROSS REFERENCE TO RELATED APPLICATIONS

This application claims the benefit of provisional U.S. patent application Ser. No. 60/362,499, filed Mar. 7, 2002.

STATEMENT OF GOVERNMENTAL INTEREST

This invention was made with government support under research Grant No. GM55600 awarded by the National Institutes for Health (NIH), Bethesda, Md. The government has certain rights in the invention.

FIELD OF THE INVENTION

The present invention relates to compounds useful as microtubule stabilizing agents. More particularly, the present invention relates to derivatives of laulimalide and the epothilones, to methods of making the compounds, and their use as microtubule stabilizing agents and as therapeutic agents, for example, in treating a cancer.

BACKGROUND OF THE INVENTION

An important and significant goal in healthcare is to discover and make available safer and more effective drugs for the treatment of cancer. Most chemotherapeutic agents act by disrupting DNA metabolism, DNA synthesis, DNA transcription, or microtubule spindle function, or by perturbing chromosomal structural integrity by introducing DNA lesions.

One important chemotherapeutic in the treatment of cancer is taxol, also known as paclitaxel, which first was isolated from the Pacific yew tree in 1971 (M. C. Wani et al., *J. Am. Chem. Soc.*, 93, 2325–2327 (1971)). Taxol enhances polymerization of tubulin and forms stable microtubule polymers. More recent studies indicate that paclitaxel binding to Bcl-2 may involve a second pathway to apoptosis.

The clinical effectiveness of taxol (1) is well recognized. Since its approval in 1992, taxol has prolonged the lives of more than 800,000 patients with ovarian, breast, and lung carcinomas. The sales of taxol in 2000 alone exceeded $1.6 billion. Recently, taxol has been approved for treatment of myeloid leukemia and has shown promise in the treatment of a number of other carcinomas, including the skin, head, and neck.

The introduction of taxol, a plant-derived anticancer agent, is an example of the importance of natural products in the treatment of complex human diseases. However, despite its clinical successes, taxol possesses a number of major limitations including: (i) debilitating side effects; (ii) poor aqueous solubility leading to complexities in its formulation; (iii) ineffectiveness against colon cancer and many other carcinomas, and critically, (iv) significant loss of therapeutic value due to the emergence of P-glycoprotein mediated multidrug-resistance (MDR), as well as drug-induced resistance-conferring tubulin mutations.

The clinical usefulness and commercial success of taxol has stimulated intense research to find other antimitotic agents that overcome many of the disadvantages associated with taxol and, therefore, provide new cancer treatments having improved therapeutic profiles. As a result, several pharmaceutical companies currently are performing clinical trials using other microtubule stabilizing agents, such as the epothilones and discodermolides.

A number of these novel natural products deviate from the taxoid platform, and still exhibit microtubule-stabilizing properties. In particular, the epothilones (A and B) and their analogs have generated interest because of a less complex structure than taxol, a minimal structural analogy to taxol, and significant biological properties (K. C. Nicolaou et al., *Agnew. Chem.*, 37, 2014–2045 (1998)).

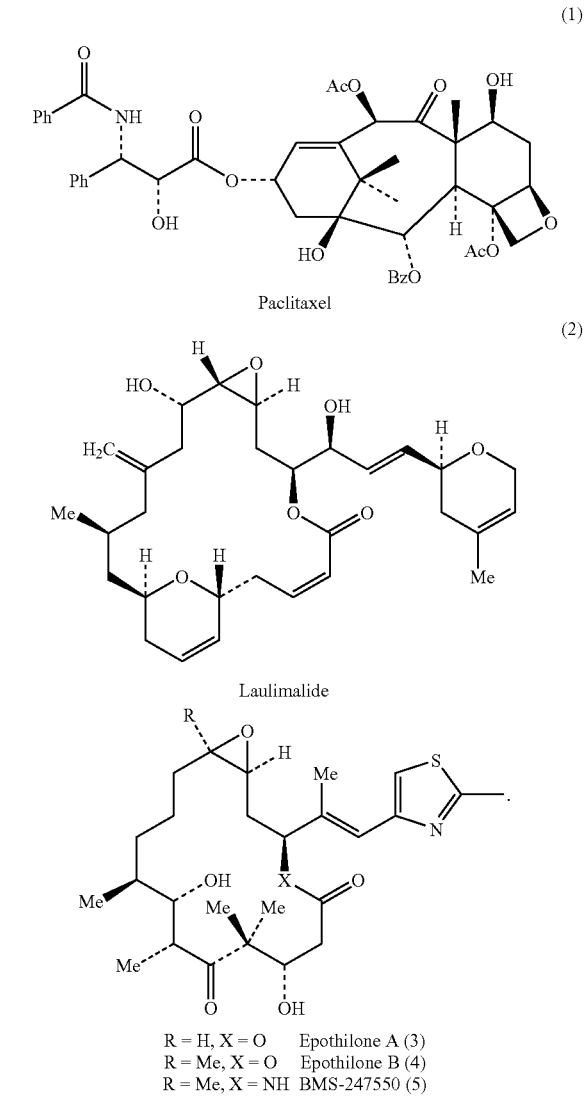

Epothilones A and B were isolated as a cytotoxic antifungal agent from a strain of myxobacteria found in soil. Subsequently, it was discovered that the epothilones stabilize microtubule assemblies and their mode of action is similar to that of taxol. Competitive binding studies indicated that the epothilones occupy a similar binding site on microtubules as [$^3$H]taxol. Furthermore, the epothilones maintain cytotoxicity against P-glycoprotein expressing MDR cells. In addition, the epothilones are active against a number of taxol-resistant cell lines.

An epothilone derivative, BMS-247550 (5), has shown improved properties compared to epothilone B and is undergoing clinical trials. Another epothilone analog, desoxyepothilone B (6), is as potent, and less toxic, than epothilone B (4). Recent in vivo studies using compound (6) showed that it is less toxic and more effective than taxol in an MX-1 human mammary carcinoma xenograft model. Discodermolide (7), another nontaxane natural product isolated from a Caribbean sponge, also has been shown to inhibit mitosis and promote tubulin assembly more potently than taxol. Compound (7) also is an effective inhibitor of cell growth in taxol-resistant cell lines. Eleutherobin (8) and a related aglycon, sarcodictyin A, also have been shown to bind to the taxol site of microtubules. However, these compounds exhibit cross resistance to taxol-resistant cell lines.

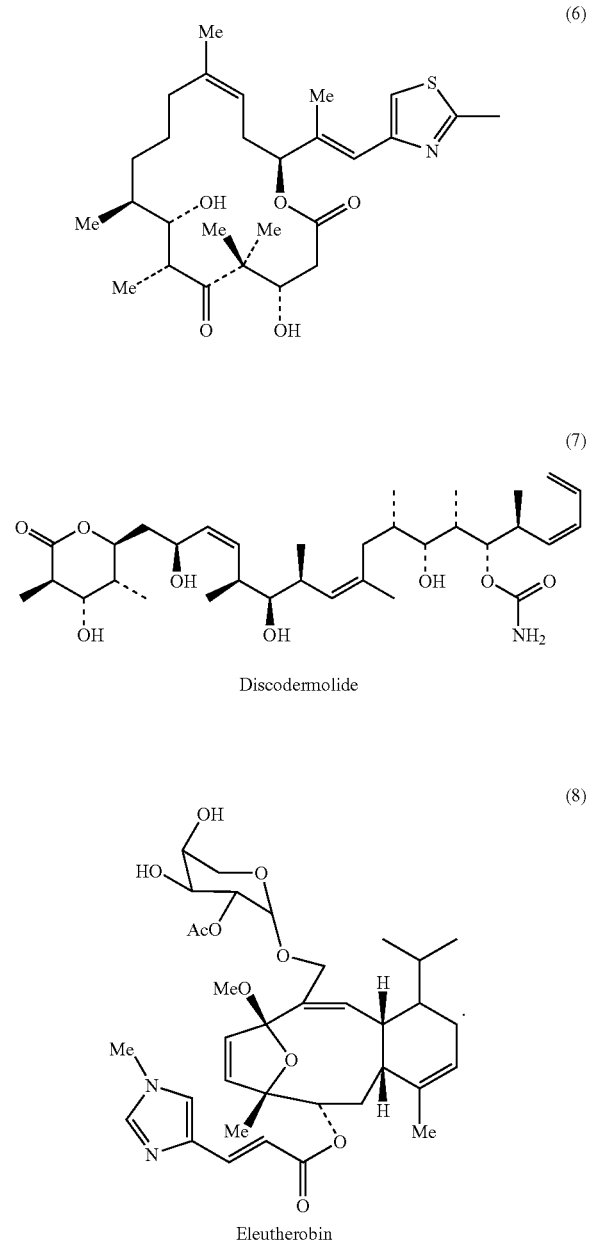

Discodermolide

Eleutherobin

Laulimalide (2), also known as figianolide B, is an 18-membered macrolide isolated in miniscule quantities from the marine sponge *Cacospongia mycofijiensis* (E. Quinoa et al., *J. Org. Chem.*, 53, 3642–4644 (1988)). Corey et al. (*J. Org. Chem.*, 53, 3644–3646 (1988)) also isolated laulimalide from the Indonesian sponge Hyattella sp. Laulimalide possesses significant antitumor properties, and has generated significant attention in recent years because laulimalide shares the same mechanism of action as taxol.

Laulimalide demonstrates potent microtubule-stabilizing properties and also displays significant antitumor properties against numerous cell lines. For example, laulimalide displays cytotoxicity against the KB cell line with an $IC_{50}$ value of 15 ng/mL, and its cytotoxicity against P388, A549, HT29, and MEL28 cell lines ranged from 10–50 ng/mL ($IC_{50}$ values). In two drug-sensitive cell lines, MDA-MB-435 and SK-OV-3, laulimalide is a potent inhibitor of cell proliferation with $IC_{50}$ values of 5–12 nM compared to 1–2 μM for taxol. Furthermore, laulimalide maintained a high level of potency against the multidrug resistant cell line SKVLB-1 ($IC_{50}$=1.2 μM). In contrast, isolaulimalide (a) is significantly less potent against the KB cell line ($IC_{50}$>200 nM) and the SKVLB-1 line ($IC_{50}$=2.6 μM). More importantly, laulimalide is 100-fold more potent than taxol against P-glycoprotein-mediated MDR cell lines.

The unique structural features, potent microtubule-stabilizing properties, and low natural abundance of laulimalide stimulated interest in its synthesis, structure-activity studies, tubulin binding properties, and molecular and cell biology. The first total synthesis of (–)-laulimalide (2) was reported in A. K. Ghosh et al., *J. Org. Chem.*, 66, 8973–8982 (2001) and A. K. Ghosh et al. *J. Am. Chem. Soc.*, 122, 11027–11029 (2000), incorporated herein by reference.

Laulimalide also has a considerable structural resemblance to the epothilones, which have generated major interest due to their activity against drug-resistant cell lines. Laulimalide shares a common pharmacophore with respect to the epothilones, yet possesses unique structural features. Based upon a structural resemblance to the epothilones, and because laulimalide possesses the same mechanism of action, it initially was hypothesized that laulimalide shared the same binding site as the epothilones. However, it now is evident that the laulimalide binding site is distinct from the binding site of taxol and the epothilones. Research already has shown that epothilones are competitive inhibitors of taxol.

The present invention is directed to compounds that provide the benefits of taxol, while overcoming various disadvantages associated with taxol, including multidrug resistance. Such compounds are analogs of laulimalide and the epothilones, and can be used in methods of treating various carcinomas, including, but not limited to, breast, refractory ovarian, small-cell lung, myeloid leukemia, metastatic carcinomas, and carcinomas of the skin, head, and neck. More particularly, the present invention is directed to more potent and less structurally complex analogs of laulimalide and the epothilones, in optically active form, that demonstrate biological activities and are useful in the treatment of cancers.

SUMMARY OF THE INVENTION

The present invention is directed to potent microtubule stabilizing agents useful in the treatment of cancers. In particular, laulimalide and epothilone derivatives have been synthesized and have demonstrated significant microtubule stabilizing activity. Accordingly, compounds of the present invention can be used in methods of treating a cancer.

In one aspect, the present invention provides compounds having general structural formulae (Ia), (Ib), (II), (III), (IV), and (V).

(Ia)
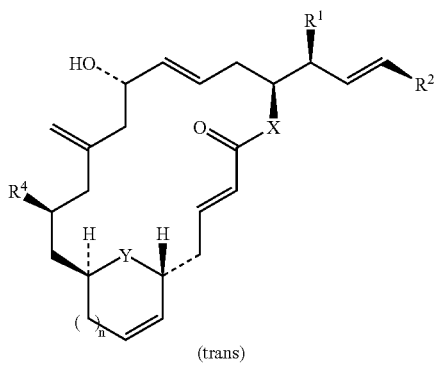
(trans)

(Ib)
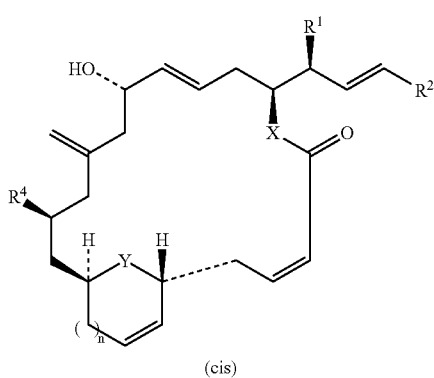
(cis)

(II)
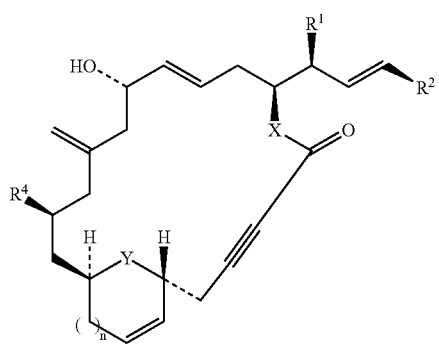

(III)
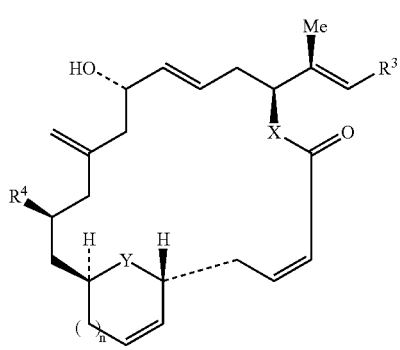

(IV)
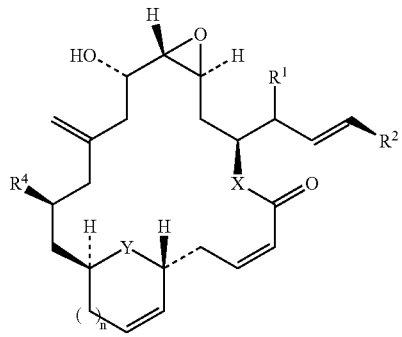

(V)
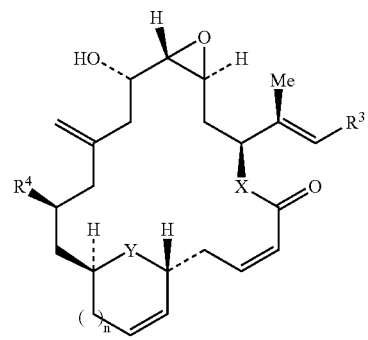

wherein $R^1$ is selected from the group consisting of hydro, $OR^a$, and $C_{1-3}$alkyl;

$R^2$ is selected from the group consisting of $C_{3-7}$heterocycloalkyl, $C_{3-7}$heterocycloalkenyl, $C_{3-7}$cycloalkyl, $C_{3-7}$cycloalkenyl, $C_{1-3}$alkyleneOR$^a$, OR$^a$, $C_{1-3}$alkyleneN(R$^a$)$_2$, N(R$^a$)$_2$, aryl, and heteroaryl;

$R^3$ is selected from the group consisting of heteroaryl, aryl, $C_{3-7}$heterocycloalkyl, and $C_{3-7}$heterocycloalkenyl;

$R^4$ is selected from the group consisting of $C_{1-4}$alkyl, OR$^a$, $C_{3-7}$cycloalkyl, $C_{3-7}$heterocycloalkyl, aryl, and heteroaryl;

X and Y, independently, are selected from the group consisting of $CH_2$, O, NR$^a$, and S;

$R^a$ is selected from the group consisting of hydro, $C_{1-4}$alkyl, $C_{2-4}$alkenyl, $C_{2-4}$alkynyl, heteroaryl, and aryl;

n is 0 or 1;

and pharmaceutically acceptable salts, solvates (e.g., hydrates), or prodrugs thereof.

The present invention also is directed to compounds having general structural formulae (VIa), (VIb), and (VII) through (XV).

(VIa)
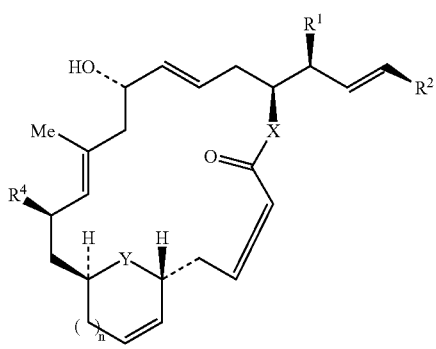

-continued
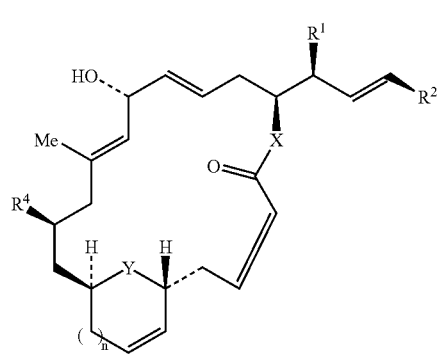
(VIb)
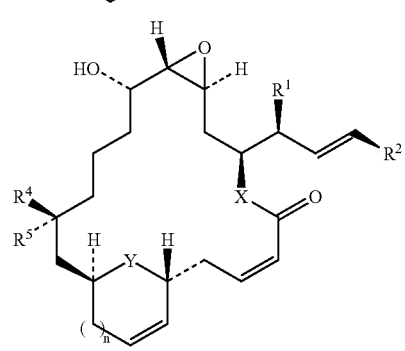
(VII)
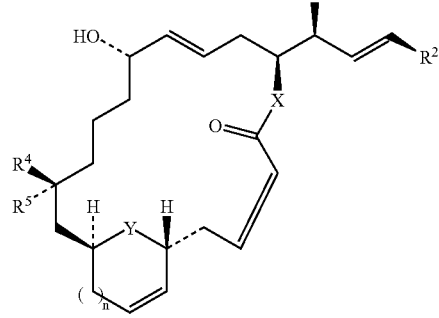
(VIII)
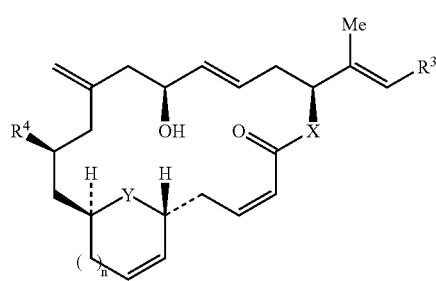
(IX)
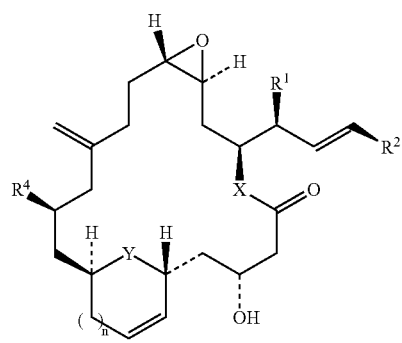
(X)
-continued
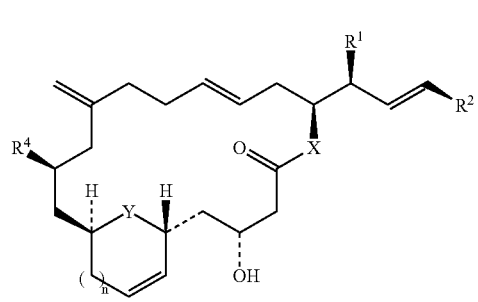
(XI)
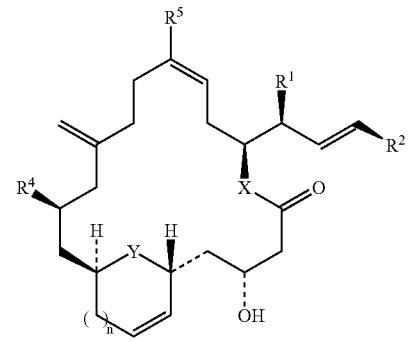
(XII)
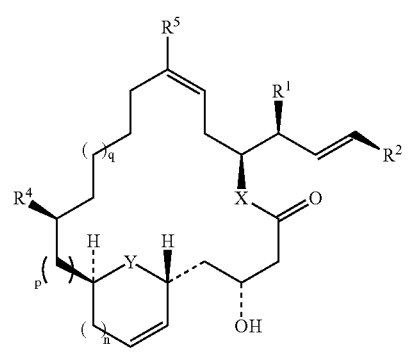
(XIII)
p = 0, 1
q = 0, 1
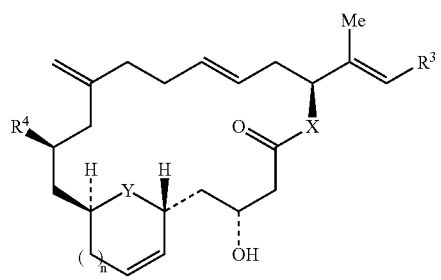
(XIV)
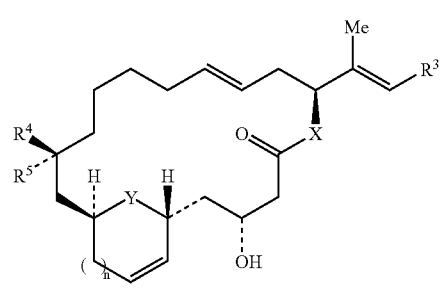
(XV)

wherein $R^1$, $R^2$, $R^3$, $R^4$, $R^a$, X, Y, and n are as defined above; $R^5$ is selected from the group consisting of hydro, $C_{1-4}$alkyl, $C_{3-7}$cycloalkyl, $C_{3-7}$heterocycloalkyl, aryl, and heteroaryl; p is 0 or 1; and q is 0 or 1, and pharmaceutically acceptable salts, solvates (e.g., hydrates), or prodrugs thereof.

Another aspect of the present invention is to provide potent microtubule stabilizing compounds useful in the treatment of a cancer. The cancer can be, for example, a breast cancer, an ovarian cancer, a lung cancer, a myeloid leukemia, a skin cancer, a head cancer, or a neck cancer.

Another aspect of the present invention is to provide methods of treating cancers by administration of a therapeutically effective amount of a compound of the present invention to an individual in need thereof.

Still another aspect of the present invention is to provide pharmaceutical compositions containing one or more compounds of the present invention, to use of the compounds and compositions containing the compounds in a therapeutic treatment of a disease or disorder, and to methods of preparing the compounds and intermediates involved in the synthesis of compounds of the present invention.

Another aspect of the present invention is to provide a microtubule stabilizing agent having an $EC_{50}$ value of about 50 μM or less, preferably about 40 μM or less, more preferably about 30 μM or less, and most preferably about 10 μM or less, e.g., down to about 0.1 nM.

Still another aspect of the present invention is to provide a method of treating an individual suffering from a disease or condition wherein stabilization of microtubules provides a benefit, said method comprising the step of administering a therapeutically effective amount of a compound of the present invention, or a composition containing the same, to the individual. The method minimizes or eliminates various adverse side effects attributed to taxol administration.

Yet another aspect of the present invention is to provide a combination therapy comprising administration of therapeutically effective amounts of (a) a compound of the present invention, or a pharmaceutically acceptable salt, prodrug, or solvate thereof, in combination with (b) a second therapeutically active agent, to an individual in need thereof, simultaneously, separately, or sequentially, for the treatment of a disease or condition wherein stabilization of microtubules provides a benefit, such as a cancer. The second therapeutically active agent can be a second microtubule stabilizing agent, a cancer chemotherapeutic agent, or radiation, for example.

Another aspect of the present invention is to provide a kit for the treatment of a cancer comprising a compound of the present invention, or a composition containing the same, packaged with instructions for administration of the compound or composition to a mammal, including a human, to treat a cancer. In one variation, the compound of the present invention and a second therapeutically active agent for the treatment of cancer are packaged together in separate vials, separate dosage forms, or the like.

Yet another aspect of the present invention is to provide an article of manufacture for human pharmaceutical use, comprising (a) a package insert, (b) a container, and either (c1) a packaged composition comprising a compound of the present invention and a second pharmaceutical agent or (c2) a packaged composition comprising a compound of the present invention and a packaged composition comprising a second pharmaceutical agent. The second pharmaceutical drug typically is useful in the treatment of a cancer.

These and other aspects of the present invention will become apparent from the following detailed description of the preferred embodiment.

DETAILED DESCRIPTION OF THE PREFERRED EMBODIMENTS

Radiation and most chemotherapeutic agents are therapeutically beneficial because they take advantage of inappropriate tumor cell proliferation. Cellular processes, such as DNA damage repair and cell cycle checkpoints, protect tumor cells from the toxic effects of physical and chemical agents. Treatments that modulate the underlying molecular mechanisms of cell cycle progression and resistance to DNA damage can potentiate tumor cell killing and enhance the therapeutic index of the therapy.

Most chemotherapeutic agents act by disrupting DNA metabolism. Because these processes are shared by both normal and tumor cells, and because the maintenance of DNA integrity is essential to cell viability, anticancer drugs have the lowest therapeutic index of any drug class. By identifying and inhibiting cellular processes that tumor cells rely upon, the effectiveness of radiation and chemotherapy treatment regimens can be enhanced. The present invention is directed to compounds that improve cancer treatment regimens by stabilizing microtubules, and reducing or overcoming problems, such as multidrug resistance, associated with prior anticancer drugs, like taxol.

A compound is considered to be a microtubule stabilizing agent if the compound effectively stabilizes microtubules at a physiologically compatible concentration. To be useful as a therapeutic compound, the agent also must not be overtly toxic to a cell at such a concentration. Effective inhibition typically is defined as a compound that stabilizes microtubules by at least 50%, preferably at least 80%, and more preferably at least 90%, at a physiologically compatible concentration.

Microtubule stabilization typically is measured using a dose-response assay in which a sensitive assay system is contacted with a compound of interest over a range of concentrations at which no or minimal effect is observed, through higher concentrations at which partial effect is observed, to saturating concentrations at which a maximum effect is observed. Theoretically, such assays of the dose-response effect of stabilizer compounds can be expressed as a curve, expressing a degree of stabilization as a function of concentration. The curve also theoretically passes through a point at which the concentration is sufficient to stabilize microtubules to a level that is 50% that of the difference between minimal and maximal activity in the assay. This concentration is defined as the Inhibitory Concentration (50%) or $IC_{50}$. Comparisons between the efficacy of stabilizers often are provided with reference to comparative $IC_{50}$ concentrations, wherein a higher $IC_{50}$ indicates that the test compound is less potent, and a lower $IC_{50}$ indicates that the compound is more potent, than a reference compound.

Similarly, the potency of stabilizer compounds can be related in terms of the Effective Concentration (50%) or $EC_{50}$, which is a measure of dose-response activity in a cell-based or animal-based model. $EC_{50}$ measurements are useful to relate properties of the compound that can influence its clinical utility, such as compound solubility, ability to penetrate cell membranes, partition coefficient, bioavailability, and the like. Two compounds can exhibit a divergence in comparative $IC_{50}$ and $EC_{50}$ values, i.e., one compound can be more potent in a biochemical assay and the second compound more potent in a cell-based assay simply due to different properties of the compounds.

A number of laulimalide and epothilone analogs useful as microtubule stabilizing agents have been synthesized and evaluated. Analogs of laulimalide and epothilone that have been synthesized, include, but are not limited to, (1) desoxylaulimalide and azadesoxylaulimalide; (2) analogs of desoxylaulimalide; and (3) analogs of desoxylaulimalide, azadesoxylaulimalide, and epothilone. One of the analogs, i.e., desoxylaulimalide (12a), has a potency similar to laulimalide (2) with respect to microtubule stabilization. These biological results are both new and unexpected in the art.

In particular, the microtubule stabilizers of the present invention have a general structural formula (Ia), (Ib), (II), (III), (IV), or (V):

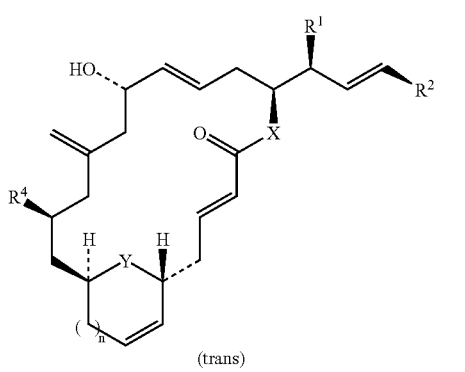
(Ia)
(trans)

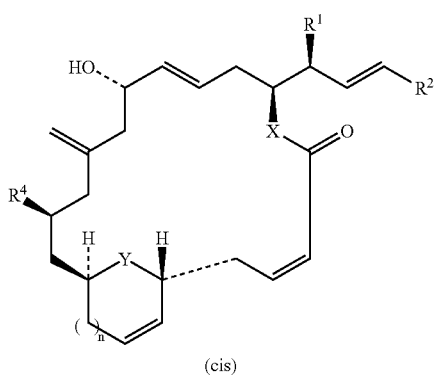
(Ib)
(cis)

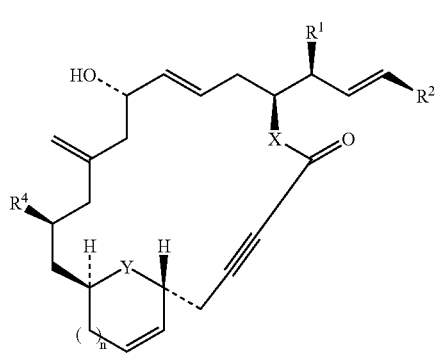
(II)

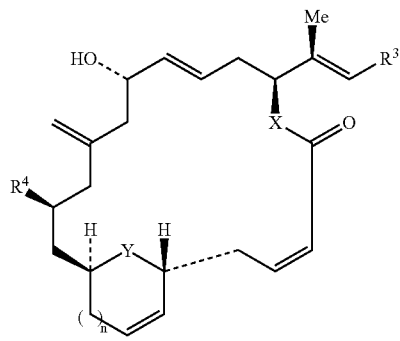
(III)

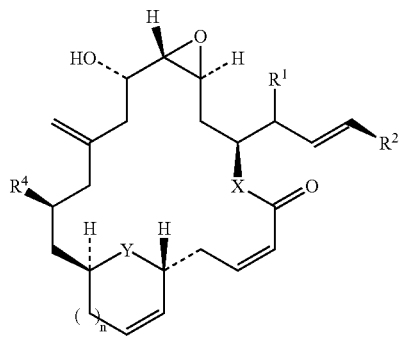
(IV)

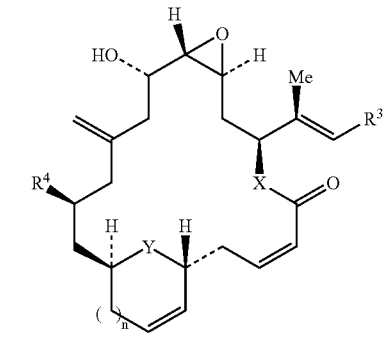
(V)

wherein $R^1$ is selected from the group consisting of hydro, $OR^a$, and $C_{1-3}$alkyl;

$R^2$ is selected from the group consisting of $C_{3-7}$heterocycloalkyl, $C_{3-7}$heterocycloalkenyl, $C_{3-7}$cycloalkyl, $C_{3-7}$cycloalkenyl, $C_{1-3}$alkyleneOR$^a$, $OR^a$, $C_{1-3}$alkyleneN(R$^a$)$_2$, N(R$^a$)$_2$, aryl, and heteroaryl;

$R^3$ is selected from the group consisting of heteroaryl, aryl, $C_{3-7}$heterocycloalkyl, and $C_{3-7}$heterocycloalkenyl;

$R^4$ is selected from the group consisting of $C_{1-4}$alkyl, $OR^a$, $C_{3-7}$cycloalkyl, $C_{3-7}$heterocycloalkyl, aryl, and heteroaryl;

X and Y, independently, are selected from the group consisting of $CH_2$, O, $NR^a$, and S;

$R^a$ is selected from the group consisting of hydro, $C_{1-4}$alkyl, $C_{2-4}$alkenyl, $C_{2-4}$alkynyl, heteroaryl, and aryl;

n is 0 or 1;

and pharmaceutically acceptable salts, solvates (e.g., hydrates), or prodrugs thereof.

Additional microtubule stabilizers of the present invention have a general structural formula (VIa), (VIb), or (VII)–(XV).

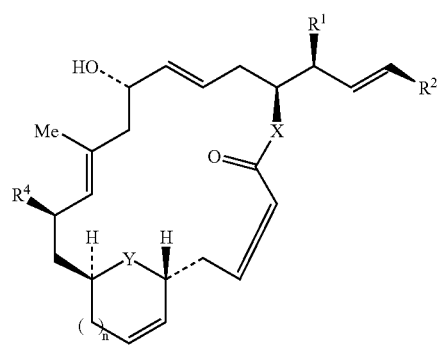
(VIa)
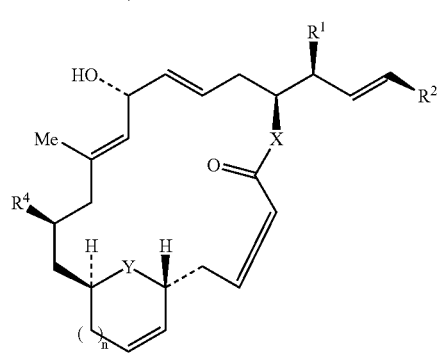
(VIb)
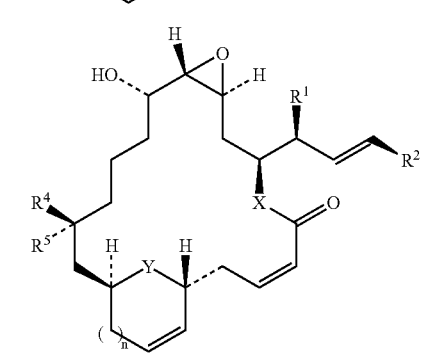
(VII)
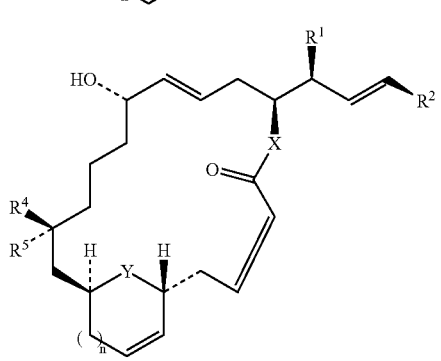
(VIII)
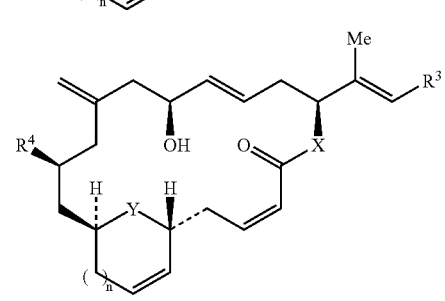
(IX)
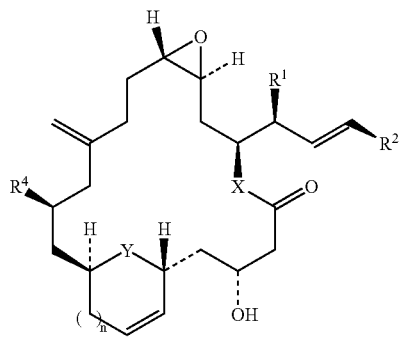
(X)
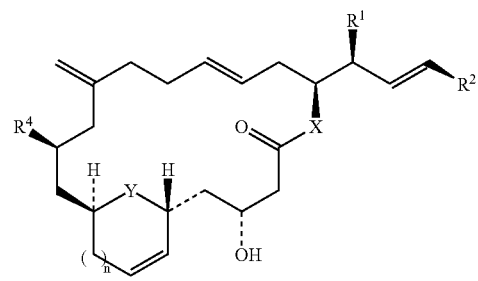
(XI)
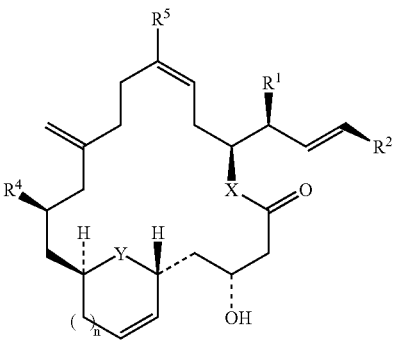
(XII)
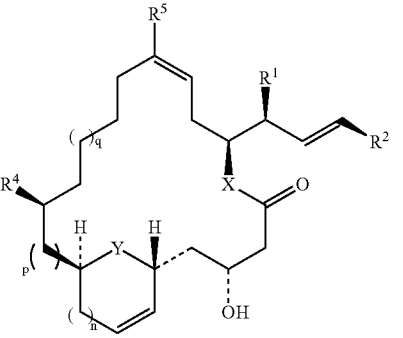
(XIII)
p = 0, 1
q = 0, 1
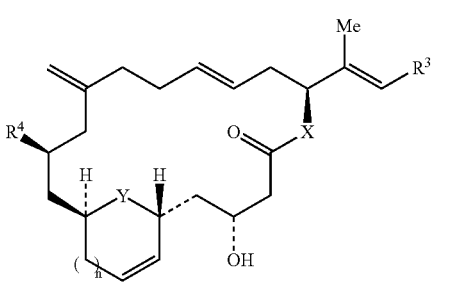
(XIV)

-continued

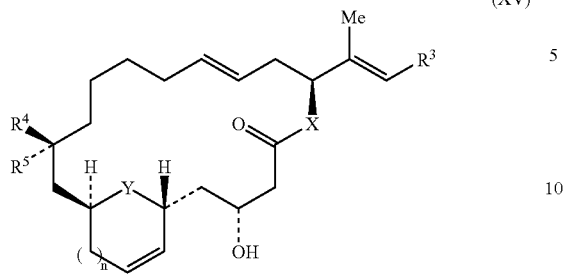
(XV)

wherein $R^1$, $R^2$, $R^3$, $R^4$, $R^a$, X, Y, and n are as defined above; $R^5$ is selected from the group consisting of hydro, $C_{1-4}$alkyl, $C_{3-7}$cycloalkyl, $C_{3-7}$heterocycloalkyl, aryl, and heteroaryl; p is 0 or 1; and q is 0 or 1, and pharmaceutically acceptable salts, solvates (e.g., hydrates), or prodrugs thereof.

In some preferred embodiments, $R^1$ is H, $OR^a$, or $CH_3$; $R^2$ is an optionally substituted five- or six-membered heterocycloalkenyl group or an optionally substituted five- or six-membered heteroaryl group; $R^3$ is an optionally substituted five- or six-membered heteroaryl group; $R^4$ is $C_{1-4}$alkyl; $R^5$ is H or $C_{1-4}$alkyl; $R^a$ is H or $C_{1-4}$alkyl; X is O or $NR^a$; and Y is O or $NR^a$.

In other preferred embodiments, $R^1$ is H or OH; $R^2$ is an optionally substituted five- or six-membered, oxygen-containing cycloalkenyl group, or an optionally substituted five- or six-membered heteroaryl group; $R^3$ is an optionally substituted five- or six-membered heteroaryl group containing sulfur and/or nitrogen atoms; $R^4$ is $CH_3$; $R^5$ is H or $CH_3$; $R^a$ is H or $CH_3$; X is O or $NR^a$; Y is O or $NR^a$; and n is 1. In such preferred embodiments, $R^2$ and $R^3$ are substituted with one or more $C_{1-3}$alkyl groups, preferably methyl or ethyl groups.

In yet other preferred embodiments, $R^1$ is H or OH; $R^2$ is

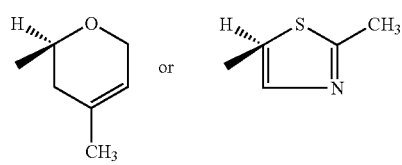

$R^3$ is

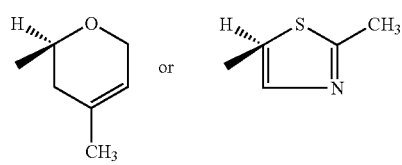

$R^4$ is H or $CH_3$; $R^5$ is $CH_3$ or H; X is O or NH; Y is O or N—$CH_3$; and n is 1.

Nonlimiting examples of microtubule stabilizing agents of the present invention, include, but are not limited to, the following compounds of structural formulae (10)–(13), (12a), (53)–(59), (66)–(71), (79)–(86), and (100)–(102).

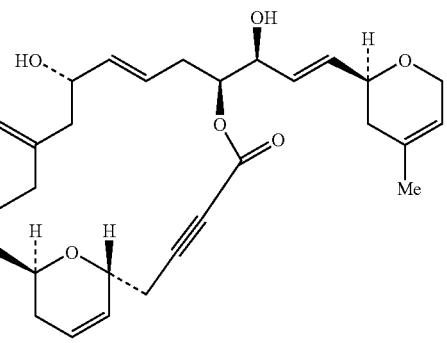
(10)

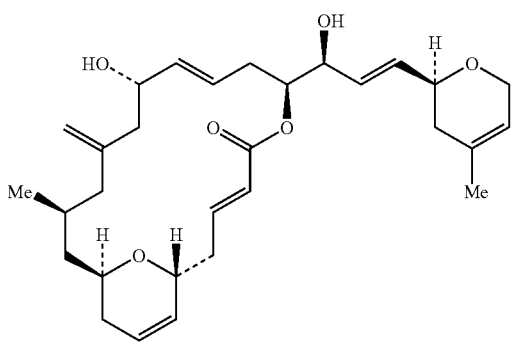
(11)

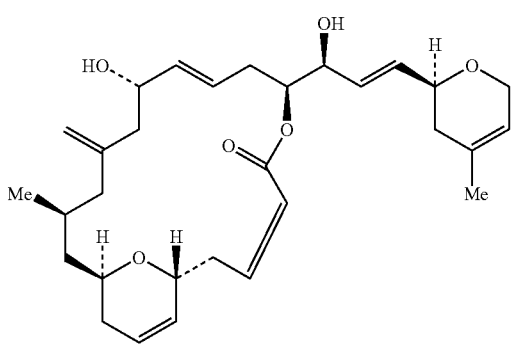
(12)

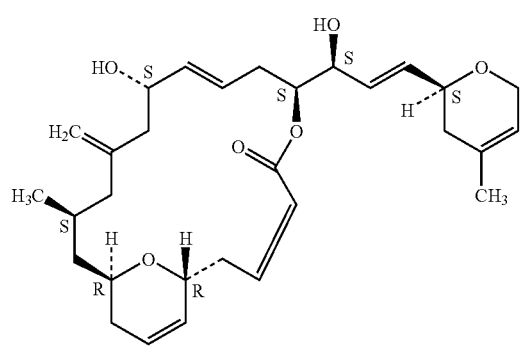
(12a)

-continued
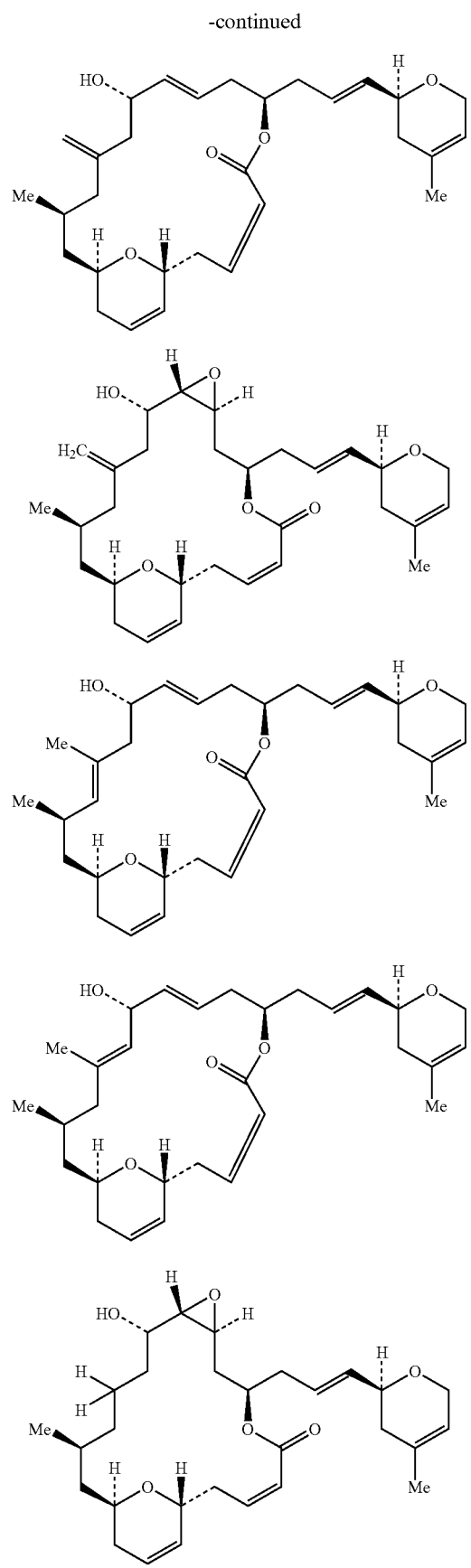
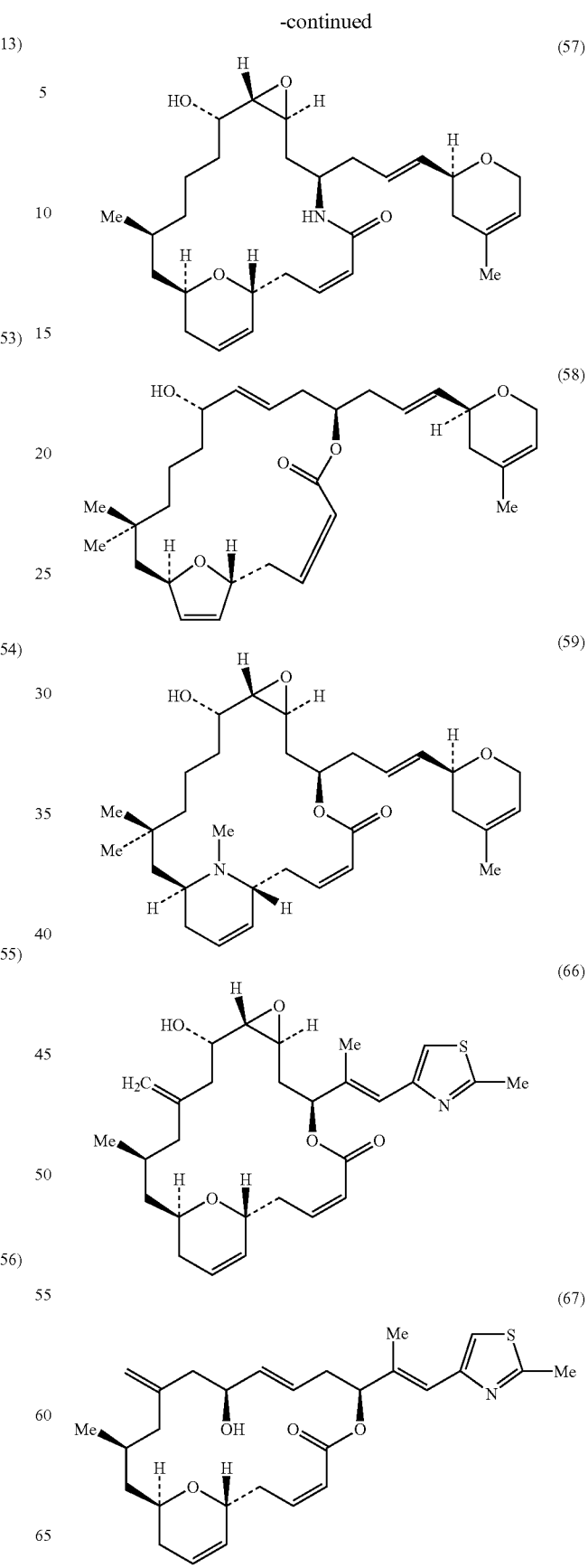

-continued
(68)
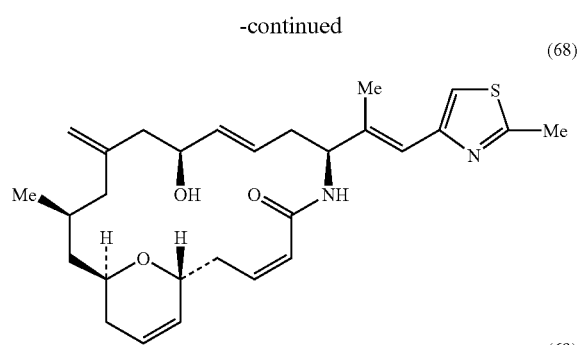
(69)
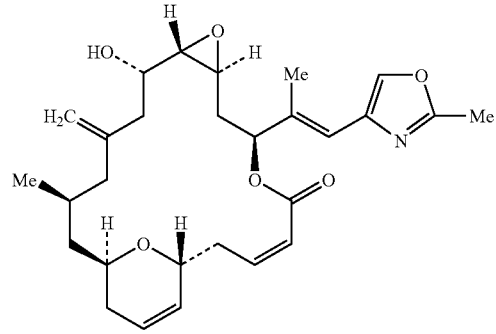
(70)
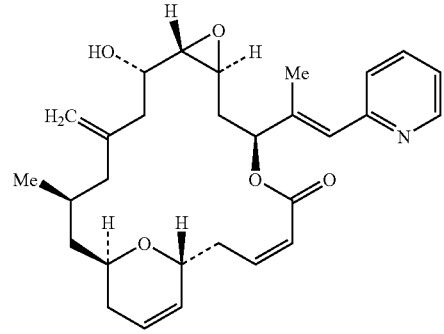
(71)
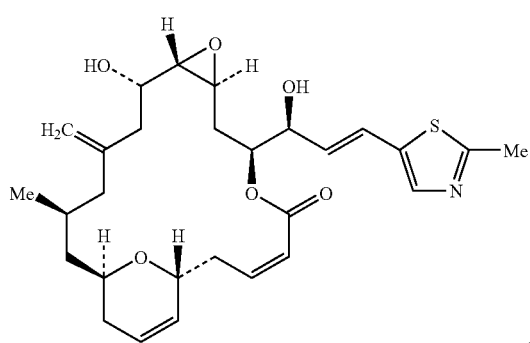
(79)
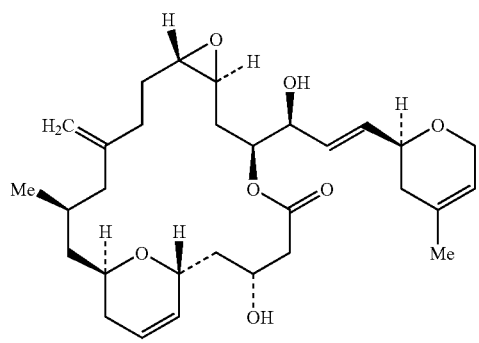
-continued
(80)
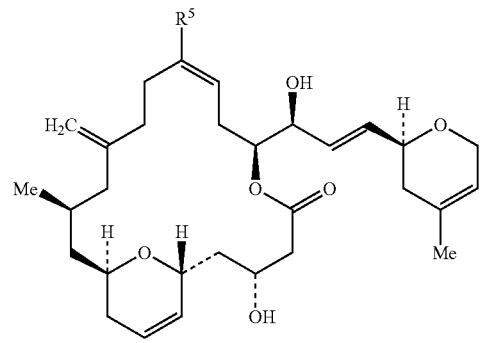
(81)
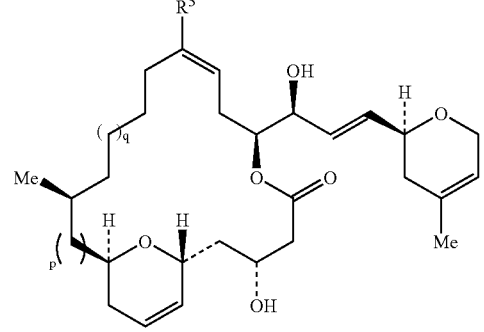
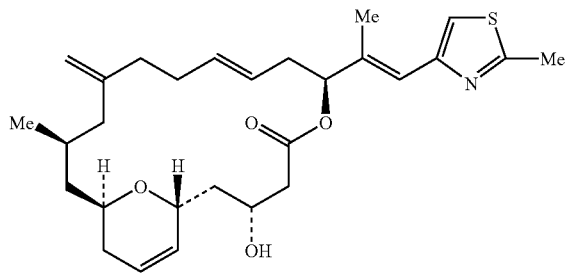
(82) p = 1, q = 1
(83) p = 0, q = 1
(84) p = 0, q = 0
(85)
(86)
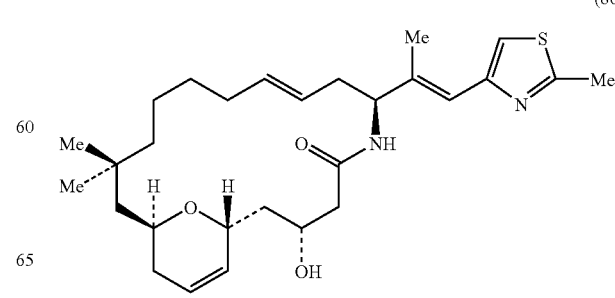

-continued (100)

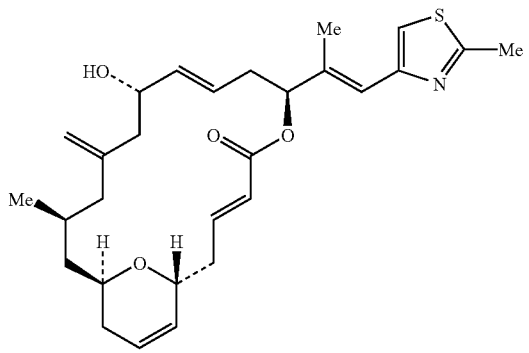

(101)

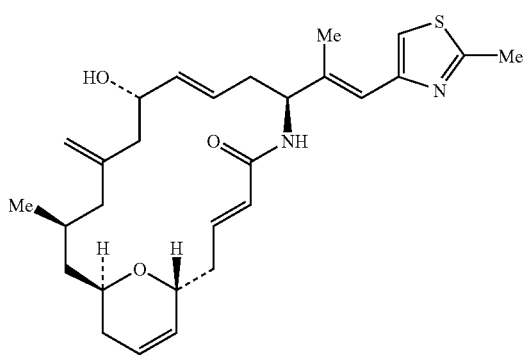

(102)

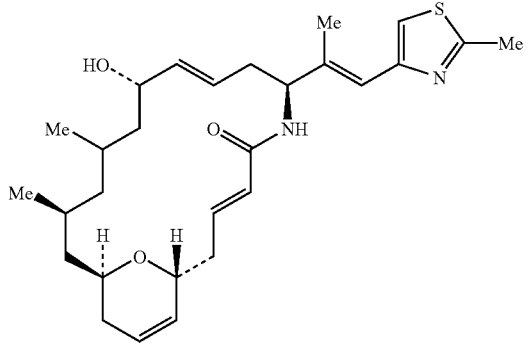

As used herein, the term "alkyl" includes straight chained and branched hydrocarbon groups containing the indicated number of carbon atoms, typically methyl, ethyl, and straight-chain and branched propyl and butyl groups. An abbreviation for methyl is Me. Unless otherwise indicated, the hydrocarbon group can contain up to 16 carbon atoms. The term "alkyl" includes "bridged alkyl," i.e., a $C_{6-16}$ bicyclic or polycyclic hydrocarbon group, for example, norbornyl, adamantyl, bicyclo[2.2.2]octyl, bicyclo[2.2.1]heptyl, bicyclo[3.2.1]octyl, or decahydronaphthyl. Alkyl groups can be substituted, for example, with hydroxy (OH), halo, aryl, heterocycloalkyl, amino ($N(R^b)_2$), and sulfonyl ($SO_2R^b$), wherein $R^b$ is selected from the group consisting of hydro, $C_{1-6}$alkyl, cycloalkyl, aryl, and $SO_2C_{1-6}$ alkyl, or two $R^b$ groups are taken together to form a 5- or 6-membered ring.

The term "alkenyl" is defined identically as "alkyl," except the substituent contains a carbon-carbon double bond.

The term "alkynyl" is defined identically as "alkyl," except the substituent contains a carbon-carbon triple bond.

The term "alkylene" refers to an alkyl group having a substituent. For example, the term "$C_{1-3}$alkyleneOH" refers to an alkyl group containing one to three carbon atoms substituted with an OH group.

The term "cycloalkyl" and "cycloalkenyl" are defined as a cyclic $C_{3-7}$ hydrocarbon group, e.g., cyclopropyl, cyclobutyl, cyclohexyl, cyclohexenyl, cyclopentenyl, and cyclopentyl. "Heterocycloalkyl" and "heterocycloalkenyl" are defined similarly as cycloalkyl except the ring contains one to three heteroatoms selected from the group consisting of oxygen, nitrogen, and sulfur. Cycloalkyl and heterocycloalkyl groups are saturated ring systems, and cycloalkenyl and heterocycloalkenyl are partially unsaturated ring systems, all optionally substituted with, for example, one to three groups, independently selected from $C_{1-4}$alkyl, $C_{1-3}$alkyleneOH, $C_{1-3}$alkyleneN($R^a$)$_2$, $NH_2$, oxo (=O), aryl, and OH.

The term "halo" is defined herein to include fluoro, bromo, chloro, and iodo.

The term "aryl," alone or in combination, is defined herein as a monocyclic or polycyclic aromatic group, preferably a monocyclic or bicyclic aromatic group, e.g., phenyl or naphthyl. Unless otherwise indicated, an "aryl" group can be unsubstituted or substituted, for example, with one or more, and in particular one to four, halo, $C_{1-6}$alkyl, $C_{2-6}$alkenyl, $OCF_3$, $NO_2$, CN, NC, $N(R^b)_2$, $OR^b$, $CO_2R^b$, $C(O)N(R^b)_2$, $C(O)R^b$, $N(R^b)COR^b$, $N(R^b)C(O)OR^b$, $N(R^b)C$—(O)$OR^b$, $N(R^b)C(O)C_{1-3}$alkyleneC(O)$R^b$, $N(R^b)C(O)C_{1-3}$alkyleneC(O)$OR^b$, $N(R^b)C(O)C_{1-3}$alkyleneO$R^b$, $N(R^b)C(O)C_{1-3}$alkyleneNHC(O)$OR^b$, $N(R^b)C(O)C_{1-3}$alkyleneSO$_2$N$R^b$, $C_{1-3}$alkyleneO$R^b$, and $SR^b$. Exemplary aryl groups include phenyl, naphthyl, tetrahydronaphthyl, chlorophenyl, methylphenyl, methoxyphenyl, trifluoromethylphenyl, nitrophenyl, 2,4-methoxychlorophenyl, and the like.

The term "heteroaryl" is defined herein as a monocyclic or bicyclic ring system containing one or two aromatic rings and containing at least one nitrogen, oxygen, or sulfur atom in an aromatic ring, and that can be unsubstituted or substituted, for example, with one or more, and in particular one to four, substituents, for example, hydrogen, $C_{1-6}$alkyl, $C_{1-6}$alkoxy, aryl, $N(R^b)_2$, $OR^b$, and halo. Examples of heteroaryl groups include, but are not limited to, thienyl, furyl, pyridyl, oxazolyl, quinolyl, isoquinolyl, indolyl, triazolyl, isothiazolyl, isoxazolyl, imidizolyl, benzothiazolyl, pyrazinyl, pyrimidinyl, thiazolyl, and thiadiazolyl. The terms "aryl$C_{1-3}$alkyl" and "heteroaryl$C_{1-3}$alkyl" are defined as an aryl or heteroaryl group having a $C_{1-3}$alkyl substituent.

The term "hydro" is defined as —H.

The term "hydroxy" is defined as —OH.

The term "5- or 6-membered ring" as used herein refers to carbocyclic and heterocyclic aromatic groups, including, but not limited to, phenyl, thiophenyl, furyl, pyrrolyl, imidazolyl, pyrimidinyl, and pyridinyl.

The term "alkoxy" is defined as —OR, wherein R is alkyl, including cycloalkyl.

The term "alkoxyalkyl" is defined as an alkyl group wherein a hydrogen has been replaced by an alkoxy group. The term "(alkylthio)alkyl" is defined similarly as alkoxyalkyl, except a sulfur atom, rather than an oxygen atom, is present.

The term "hydroxyalkyl" is defined as a hydroxy group appended to an alkyl group.

The term "amino" is defined as —NH$_2$, and the term "alkylamino" is defined as —NR$_2$, wherein at least one R is alkyl and the second R is alkyl or hydrogen.

The term "alkylthio" and "arylthio" are defined as —SR, wherein R is alkyl or aryl, respectively.

The term "alkylsulfinyl" is defined as R—SO$_2$, wherein R is alkyl.

The term "alkylsulfonyl" is defined as R—SO$_3$, wherein R is alkyl.

The term "nitro" is defined as —NO$_2$.

The term "trifluoromethyl" is defined as —CF$_3$.

The term "trifluoromethoxy" is defined as —OCF$_3$.

The term "cyano" is defined as —CN.

The carbon atom content of hydrocarbon-containing moieties is indicated by a subscript designating the minimum and maximum number of carbon atoms in the moiety, e.g., "C$_{1-6}$alkyl" refers to an alkyl group having one to six carbon atoms, inclusive.

In the structures herein, for a bond lacking a substituent, the substituent is methyl or methylene, for example,

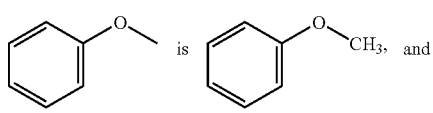

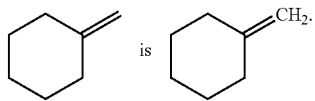

When no substituent is indicated as attached to a carbon atom on a ring, it is understood that the carbon atom contains the appropriate number of hydrogen atoms. In addition, when no substituent is indicated as attached to a carbonyl group or a nitrogen atom, for example, the substituent is understood to be hydrogen, e.g.,

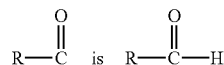

and R—N is R—NH$_2$

The notation N(R$^b$)$^2$ is used to denote two R$^b$ groups attached to a common nitrogen atom. When used in such notation, the R$^b$ group can be the same or different, and is selected from the group as defined by the R$^b$ group.

Nonlimiting examples of aryl and heteroaryl ring systems useful in compounds of the present invention include, but are not limited to,

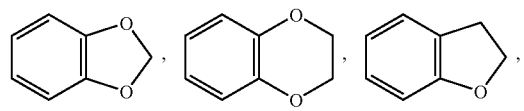

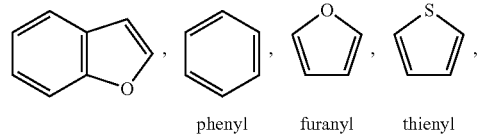

phenyl    furanyl    thienyl

-continued

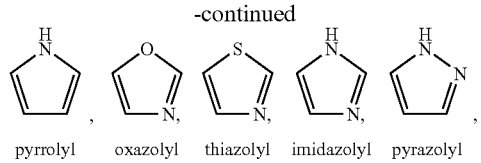

pyrrolyl    oxazolyl    thiazolyl    imidazolyl    pyrazolyl

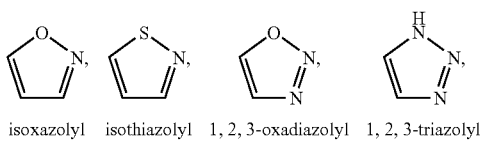

isoxazolyl    isothiazolyl    1,2,3-oxadiazolyl    1,2,3-triazolyl

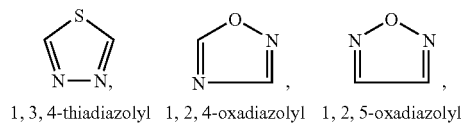

1,3,4-thiadiazolyl    1,2,4-oxadiazolyl    1,2,5-oxadiazolyl

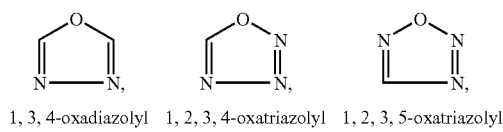

1,3,4-oxadiazolyl    1,2,3,4-oxatriazolyl    1,2,3,5-oxatriazolyl

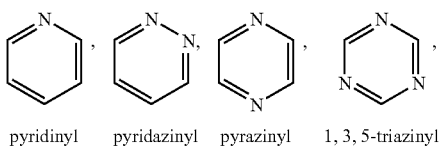

pyridinyl    pyridazinyl    pyrazinyl    1,3,5-triazinyl

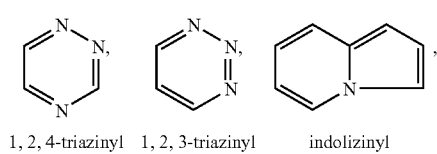

1,2,4-triazinyl    1,2,3-triazinyl    indolizinyl

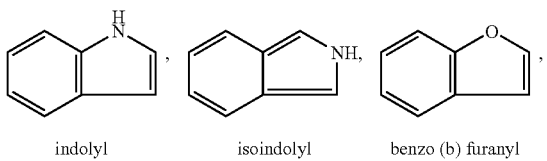

indolyl    isoindolyl    benzo(b)furanyl

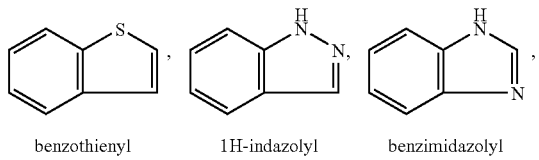

benzothienyl    1H-indazolyl    benzimidazolyl

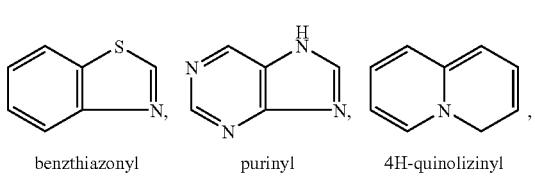

benzthiazonyl    purinyl    4H-quinolizinyl

-continued

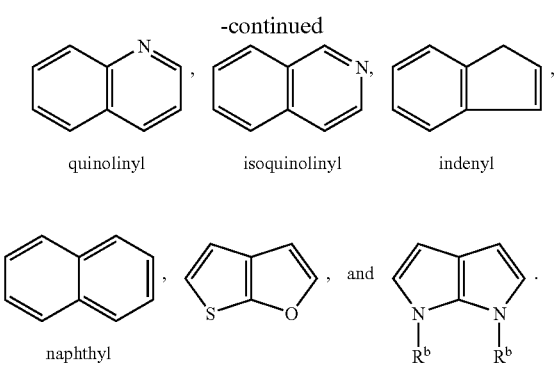

quinolinyl    isoquinolinyl    indenyl naphthyl

Nonlimiting examples of cycloalkyl, cycloalkenyl, heterocycloalkyl, and heterocycloalkenyl ring systems useful in compounds of the present invention include, but are not limited to,

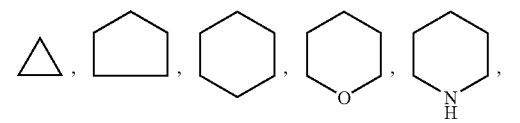

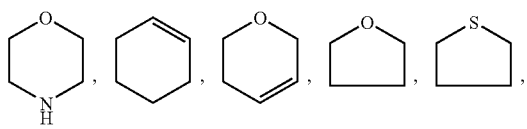

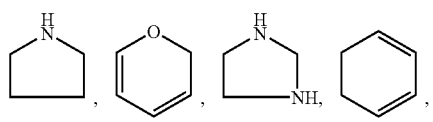

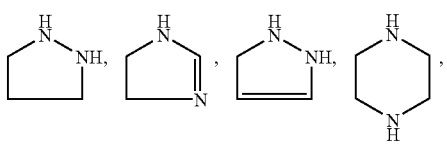

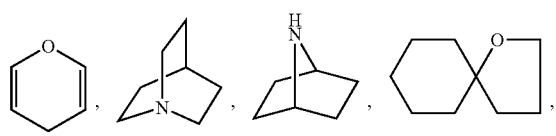

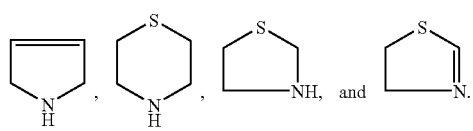

A compound of the present invention can be therapeutically administered as the neat chemical, but it is preferable to administer the compound as a pharmaceutical composition or formulation. Therefore, the present invention also is directed to pharmaceutical compositions useful for stabilizing microtubules, said compositions comprising a compound of the present invention and a pharmaceutically acceptable carrier. The carriers are "acceptable" in the sense of being compatible with the other ingredients of the formulation and not deleterious to the recipient thereof.

These pharmaceutical compositions are useful for treating cancers and other conditions wherein microtubule stabilization provides a benefit. The present invention also is directed to methods of stabilizing microtubules, methods of treating conditions wherein microtubule stabilization provides a benefit, and methods of treating a cancer comprising administration of a therapeutically effective amount of a compound of the present invention, or a composition containing a compound of the present invention, to an individual in need thereof.

Additionally, the present invention is directed to a pharmaceutical composition comprising a compound of the present invention and a chemotherapeutic agent. A microtubule stabilizer of the present invention and the chemotherapeutic agent can be formulated as separate compositions that are administered at substantially the same time, i.e., simultaneously or sequentially, or the therapeutic agents can be administered from a single composition, such that all of the active agents are present in the host in a therapeutically effective amount. Alternatively, the therapeutic agents can be administered to the host at different times, i.e., separately, such that only one or two active agents at a time are present in the host in a therapeutically effective amount.

As used herein, the term "composition" is intended to encompass a product comprising the specified ingredients in the specified amounts, as well as any product which results directly, or indirectly, from admixing the specified ingredients in the specified amounts. Thus, the invention also provides a process of preparing a pharmaceutical composition comprising a compound of the present invention comprising and mixing the compound with a pharmaceutically acceptable diluent or carrier therefor. Further provided are articles of manufacture comprising a compound of the present invention and a second pharmaceutical drug, packaged separately or together, and an insert having instructions for using the active agents.

The present invention also is directed to a method of treating a cancer comprising administration of a therapeutically effective amount of a compound of the present invention and administration of therapeutically effective amount of radiation to an individual in need thereof. The compound of the present invention and the radiation can be administered simultaneously or sequentially.

Compounds of the present invention contain one or more asymmetric center, and, therefore, can exist as stereoisomers. The present invention includes both mixtures and separate individual stereoisomers of the compounds of the present invention. Compounds of the present invention also may exist in tautomeric forms, and the invention includes both mixtures and separate individual tautomers thereof.

Pharmaceutically acceptable salts of compounds of the present invention can be acid addition salts formed with pharmaceutically acceptable acids. Examples of suitable salts include, but are not limited to, the hydrochloride, hydrobromide, sulfate, bisulfate, phosphate, hydrogen phosphate, acetate, benzoate, succinate, fumarate, maleate, lactate, citrate, tartrate, gluconate, methanesulfonate, benzenesulfonate, and p-toluenesulfonate salts. The compounds of the present invention also can provide pharmaceutically acceptable metal salts, in particular alkali metal salts, alkaline earth metal salts, and amine salts, with bases. Examples include the ammonium, alkylammonium, sodium, potassium, magnesium, and calcium salts. In light of the foregoing, any reference to compounds of the present invention appearing herein is intended to include compounds of the invention, as well as pharmaceutically acceptable salts, prodrugs, and solvates thereof.

The term "prodrug" as used herein refers to compounds that are transformed in vivo to a compound of the present invention, for example, by hydrolysis. Prodrug design is discussed generally in Hardma et al. (Eds.), *Goodman and Gilman's The Pharmacological Basis of Therapeutics,* 9th ed., pp. 11–16 (1996). A thorough discussion is provided in Higuchi et al., *Prodrugs as Novel Delivery Systems, Vol.* 14, ASCD Symposium Series, and in Roche (ed.), *Bioreversible Carriers in Drug Design,* American Pharmaceutical Association and Pergamon Press (1987). Typically, administration of a drug is followed by elimination from the body or some biotransformation whereby the biological activity of the drug is reduced or eliminated. Alternatively, a biotransformation process can lead to a metabolic by-product that is more or equally active compared to the drug initially administered. Increased understanding of these biotransformation processes permits the design of so-called "prodrugs," which, following a biotransformation, become more physiologically active in their altered state. Prodrugs, therefore, encompass compounds that are converted to pharmacologically active metabolites.

To illustrate, prodrugs can be converted into a pharmacologically active form through hydrolysis of, for example, an ester or amide linkages thereby introducing or exposing a functional group on the resultant product. The prodrugs can be designed to react with an endogenous compound to form a water-soluble conjugate that further enhances the pharmacological properties of the compound, for example, increased circulatory half-life. Alternatively, prodrugs can be designed to undergo covalent modification on a functional group with, for example, glucuronic acid, sulfate, glutathione, an amino acid, or acetate. The resulting conjugate can be inactivated and excreted in the urine, or rendered more potent than the parent compound. High molecular weight conjugates also can be excreted into the bile, subjected to enzymatic cleavage, and released back into the circulation, thereby effectively increasing the biological half-life of the originally administered compound.

Compounds of the present invention have demonstrated activity in stabilizing microtubules. Compounds of the present invention can be used alone or in combination with radiation and/or chemotherapeutics used in the treatment of cancers and other cell proliferation disorders in humans or animals. Accordingly, cancers such as ovarian cancers, skin cancers, head cancers, neck cancers, breast cancers, myeloid leukemias, and lung cancers are susceptible to treatment with a microtubule stabilizer of the present invention.

Accordingly, the present invention provides pharmaceutical formulations comprising a compound of the present invention, or a pharmaceutically acceptable salt or prodrug thereof, together with one or more pharmaceutically acceptable carriers and, optionally, other therapeutic and/or prophylactic ingredients.

Compounds and pharmaceutical compositions suitable for use in the present invention include those wherein the active ingredient is administered in an effective amount to achieve its intended purpose. More specifically, a "therapeutically effective amount" means an amount effective to inhibit development of, or to alleviate the existing symptoms of, the individual being treated. Determination of the effective amount is well within the capability of those skilled in the art, especially in light of the detailed disclosure provided herein.

A "therapeutically effective dose" refers to that amount of the compound that results in achieving the desired effect. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio of $LD_{50}$ to $ED_{50}$. Compounds that exhibit high therapeutic indices (i.e., a toxic dose that is substantially higher than the effective dose) are preferred. The data obtained can be used in formulating a dosage range for use in humans. The dosage of such compounds preferably lies within a range of circulating concentrations that include the $ED_{50}$ with little or no toxicity. The dosage can vary within this range depending upon the dosage form employed, and the route of administration utilized.

The exact formulation, route of administration, and dosage is chosen by the individual physician in view of the patient's condition. Dosage amount and interval can be adjusted individually to provide plasma levels of the active compound that are sufficient to maintain desired therapeutic effects.

Compounds of the present invention can be used in combination with radiation and chemotherapy treatment, including induction chemotherapy, primary (neoadjuvant) chemotherapy, and both adjuvant radiation therapy and adjuvant chemotherapy. In addition, radiation and chemotherapy are frequently indicated as adjuvants to surgery in the treatment of cancer. The goal of radiation and chemotherapy in the adjuvant setting is to reduce the risk of recurrence and enhance disease-free survival when the primary tumor has been controlled. Chemotherapy is utilized as a treatment adjuvant for lung and breast cancer, frequently when the disease is metastatic. Adjuvant radiation therapy is indicated in several diseases including lung and breast cancers. Compounds of the present invention also are useful following surgery in the treatment of cancer in combination with radio- and/or chemotherapy.

Chemotherapeutic agents that can be used in combination with a microtubule stabilizer of the present invention include, but are not limited to, alkylating agents, antimetabolites, hormones and antagonists, radioisotopes, antibodies, as well as natural products, and combinations thereof. For example, an inhibitor compound of the present invention can be administered with antibiotics, such as doxorubicin and other anthracycline analogs, nitrogen mustards, such as cyclophosphamide, pyrimidine analogs such as 5-fluorouracil, cisplatin, hydroxyurea, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH) Other antineoplastic protocols include the use of an inhibitor compound with another treatment modality, e.g., surgery or radiation, also referred to herein as "adjunct anti-neoplastic modalities." Examples of chemotherapeutic agents useful for the method of the present invention are listed in the following table.

| Alkylating agents | Natural products | Anthracenedione |
|---|---|---|
| Nitrogen mustards | Antimitotic drugs | mitoxantrone |
| mechlorethamine | paclitaxel | Substituted urea |
| cyclophosphamide | Vinca alkaloids | hydroxyurea |
| ifosfamide | vinblastine (VLB) | Methylhydrazine |
| melphalan | vincristine | derivatives |
| chlorambucil | vinorelbine | N-methylhydrazine (MIH) |
| Nitrosoureas | Taxotere ® (docetaxel) | procarbazine |
| carmustine (BCNU) | estramustine | Adrenocortical |
| lomustine (CCNU) | estramustine phosphate | suppressant |
| semustine (methyl-CCNU) | Epipodophylotoxins | mitotane (o,p'-DDD) |
| Ethylenimine/Methylmelamine | etoposide | aminoglutethimide |
| thriethylenemelamine (TEM) | teniposide | Cytokines |
| triethylene | Antibiotics | interferon (*, *, *) |
| thiophosphoramide | actimomycin D | interleukin-2 |
| (thiotepa) | daunomycin | Hormones and antagonists |
| hexamethylmelamine (HMM, | (rubidomycin) | Adrenocorticosteroids/ |
| altretamine) | doxorubicin | antagonists |
| Alkyl sulfonates | (adriamycin) | prednisone and |
| busulfan | mitoxantrone | equivalents |
| Triazines | idarubicin | dexamethasone |
| dacarbazine (DTIC) | bleomycins | aminoglutethimide |
| Antimetabolites | plicamycin | Progestins |
| Folic Acid analogs | (mithramycin) | hydroxyprogesterone |
| methotrexate | mitomycinC | caproate |
| trimetrexate | dactinomycin | medroxyprogesterone |
| Pyrimidine analogs | Enzymes | acetate |
| 5-fluorouracil | L-asparaginase | megestrol acetate |
| fluorodeoxyuridine | Biological response | Estrogens |
| gemcitabine | modifiers | diethylstilbestrol |
| cytosine arabinoside | interferon-alpha | ethynyl estradiol/ |
| (AraC, cytarabine) | IL-2 | equivalents |
| 5-azacytidine | G-CSF | Antiestrogen |
| 2,2'-difluorodeoxycytidine | GM-CSF | tamoxifen |
| Purine analogs | Differentiation Agents | Androgens |
| 6-mercaptopurine | retinoic acid | testosterone propionate |
| 6-thioguanine | derivatives | fluoxymesterone/equivalents |
| azathioprine | Radiosensitizers | Antiandrogens |
| 2'-deoxycoformycin | metronidazole | flutamide |
| (pentostatin) | misonidazole | gonadotropin-releasing |
| erythrohydroxynonyladenine | desmethylmisonidazole | hormone analogs |
| (EHNA) | pimonidazole | leuprolide |
| fludarabine phosphate | etanidazole | Nonsteroidal |
| 2-chlorodeoxyadenosine | nimorazole | antiandrogens |
| (cladribine, 2-CdA) | RSU 1069 | flutamide |
| Type I Topoisomerase | EO9 | Photosensitizers |
| Inhibitors | RB 6145 | hematoporphyrin |
| camptothecin | SR4233 | derivatives |
| topotecan | nicotinamide | Photofrin ® |
| irinotecan | 5-bromodeoxyuridine | benzoporphyrin |
| | 5-iododeoxyuridine | derivatives |
| | bromodeoxycytidine | Npe6 |

| -continued | |
|---|---|
| Miscellaneous agents | tin etioporphyrin (SnET2) |
| Platinium coordination complexes | pheoboride-a<br>bacteriochlorophyll-a |
| cisplatin<br>carboplatin | naphthalocyanines<br>phthalocyanines<br>zinc phthalocyanines |

Examples of chemotherapeutic agents that are particularly useful in conjunction with radio-sensitizers include, for example, adriamycin, camptothecin, carboplatin, cisplatin, daunorubicin, doxorubicin, interferon (alpha, beta, gamma), interleukin 2, irinotecan, docetaxel, topotecan, and therapeutically effective analogs and derivatives of the same.

As used above and hereafter, the term "treatment" includes preventing, lowering, stopping, or reversing the progression or severity of the condition or symptoms being treated. As such, the term "treatment" includes both medical therapeutic and/or prophylactic administration, as appropriate, including, but not limited to, the diseases and conditions discussed above.

The term "container" means any receptacle and closure therefore suitable for storing, shipping, dispensing, and/or handling a pharmaceutical product.

The term "insert" means information accompanying a product that provides a description of how to administer the product, along with the safety and efficacy data required to allow the physician, pharmacist, and patient to make an informed decision regarding use of the product. The package insert generally is regarded as the "label" for a pharmaceutical product.

The terms "administration of" and "administering a" compound should be understood to mean providing a compound of the invention or a prodrug of a compound of the invention to an individual in need of treatment.

It is further appreciated that the amount of a compound of the invention required for use in treatment varies with the nature of the condition being treated, and with the age and the condition of the patient, and is ultimately determined by the attendant physician or veterinarian. In general, however, doses employed for adult human treatment typically are in the range of 0.001 to about 100 mg/kg per day. The desired dose can be conveniently administered in a single dose, or as multiple doses administered at appropriate intervals, for example as two, three, four or more subdoses per day. In practice, the physician determines the actual dosing regimen most suitable for an individual patient, and the dosage varies with the age, weight, and response of the particular patient. The above dosages are exemplary of the average case, but there can be individual instances in which higher or lower dosages are merited, and such are within the scope of the present invention.

Formulations of the present invention can be administered in a standard manner for the treatment of the indicated diseases, such as orally, parenterally, transmucosally (e.g., sublingually or via buccal administration), topically, transdermally, rectally, via inhalation (e.g., nasal or deep lung inhalation). Parenteral administration includes, but is not limited to intravenous, intraarterial, intraperitoneal, subcutaneous, intramuscular, intrathecal, and intraarticular. Parenteral administration also can be accomplished using a high pressure technique, like POWDERJECT™.

For oral administration, including buccal administration, the composition can be in the form of tablets or lozenges formulated in conventional manner. For example, tablets and capsules for oral administration can contain conventional excipients such as binding agents (for example, syrup, acacia, gelatin, sorbitol, tragacanth, mucilage of starch, or polyvinylpyrrolidone), fillers (for example, lactose, sugar, microcrystalline cellulose, maize-starch, calcium phosphate, or sorbitol), lubricants (for example, magnesium stearate, stearic acid, talc, polyethylene glycol or silica), disintegrates (for example, potato starch or sodium starch glycolate), or wetting agents (for example, sodium lauryl sulfate). The tablets can be coated according to methods well known in the art.

Alternatively, the compounds of the present invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, for example suspending agents, such as sorbitol syrup, methyl cellulose, glucose/sugar syrup, gelatin, hydroxyethylcellulose, hydroxypropylmethylcellulose, carboxymethylcellulose, aluminum stearate gel, and hydrogenated edible fats; emulsifying agents, such as lecithin, sorbitan monooleate, or acacia; nonaqueous vehicles (which can include edible oils), such as almond oil, fractionated coconut oil, oily esters, propylene glycol, and ethyl alcohol; and preservatives, such as methyl or propyl p-hydroxybenzoate and sorbic acid.

Such preparations also can be formulated as suppositories, e.g., containing conventional suppository bases, such as cocoa butter or other glycerides. Compositions for inhalation typically can be provided in the form of a solution, suspension, or emulsion that can be administered as a dry powder or in the form of an aerosol using a conventional propellant, such as dichlorodifluoromethane or trichlorofluoromethane. Typical topical and transdermal formulations comprise conventional aqueous or nonaqueous vehicles, such as eye drops, creams, ointments, lotions, and pastes, or are in the form of a medicated plaster, patch, or membrane.

Additionally, compositions of the present invention can be formulated for parenteral administration by injection or continuous infusion. Formulations for injection can be in the form of suspensions, solutions, or emulsions in oily or aqueous vehicles, and can contain formulation agents, such as suspending, stabilizing, and/or dispersing agents. Alternatively, the active ingredient can be in powder form for constitution with a suitable vehicle (e.g., sterile, pyrogen-free water) before use.

A composition in accordance with the present invention also can be formulated as a depot preparation. Such long acting formulations can be administered by implantation (for example, subcutaneously or intramuscularly) or by intramuscular injection. Accordingly, the compounds of the invention can be formulated with suitable polymeric or hydrophobic materials (e.g., an emulsion in an acceptable oil), ion exchange resins, or as sparingly soluble derivatives (e.g., a sparingly soluble salt).

The present invention also is directed to a method of treating conditions and disorders wherein microtubule stabilization provides a benefit, in a human or nonhuman animal body, comprising administering a therapeutically effective amount of a compound of the present invention to said body.

In vivo methods of treatment are specifically contemplated. Thus, for example, the present invention includes a method of treating cancer in a mammal comprising the steps of administering to the mammal (a) a compound of the present invention to stabilize microtubules and (b) an optional second active compound or agent for treating a cancer, wherein the compound or compounds are administered at concentrations effective to treat a cancer in the mammal. Administration to humans is specifically contemplated, but administration to other animals, including pets, livestock, zoo specimens, wildlife, and the like, also is contemplated.

For veterinary use, a compound of the present invention, or a nontoxic salt or prodrug thereof, is administered as a suitably acceptable formulation in accordance with normal veterinary practice. The veterinarian can readily determine the dosing regimen and route of administration that is most appropriate for a particular animal.

Specific, nonlimiting examples of compounds of the present invention are provided below as compounds of general structural formulae (I) through (X), the synthesis of which were performed in accordance with the procedures set forth hereafter.

Generally, compounds of the present invention can be prepared according to the synthetic scheme set forth below. In the scheme described herein, it is understood in the art that protecting groups can be employed where necessary in accordance with general principles of synthetic chemistry. These protecting groups are removed in the final steps of the synthesis under basic, acidic, or hydrogenolytic conditions which are readily apparent to those skilled in the art. By employing appropriate manipulation and protection of any chemical functionalities, synthesis of compounds of the present invention not specifically set forth herein can be accomplished by methods analogous to the schemes set forth below.

The syntheses of various compounds of the present invention are set forth below:

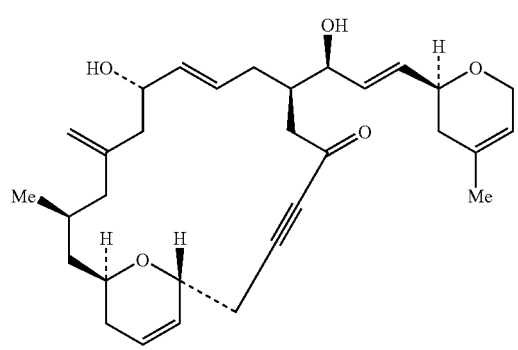
(10)

-continued

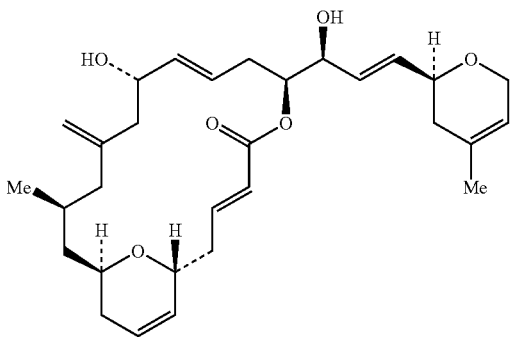
(11)

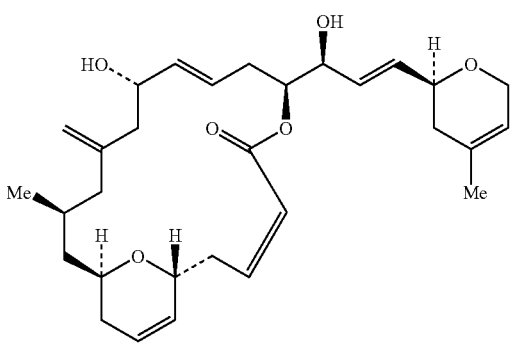
(12)

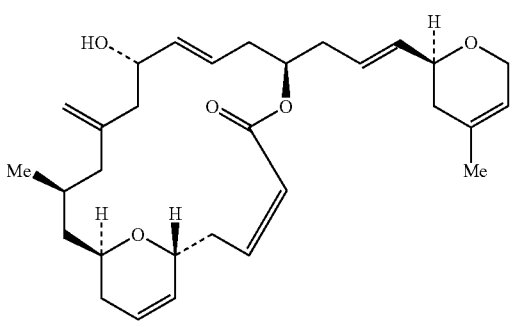
(13)

Preparation of Laulimalide Analogs (10–13) and (53)

The detailed synthesis of various intermediates and precursors discussed herein can be found in A. Ghosh et al., *J. Org. Chem.*, 66, 8973–8982 (2001), incorporated herein by reference.

Laulimalide analogs (10–12) were prepared from the corresponding $C_{15}$- and $C_{20}$-hydroxyl protected derivatives (39), (36), and (37). The $C_{15}$-MOM group was removed by heating with pyridinium p-toluenesulfonate (PPTS) in tertiary-butyl alcohol (t-BuOH) at reflux. The resulting alcohols were treated with DDQ in pH 7 buffer to provide compounds (10–12) (about 1 mg each) for biological evaluation.

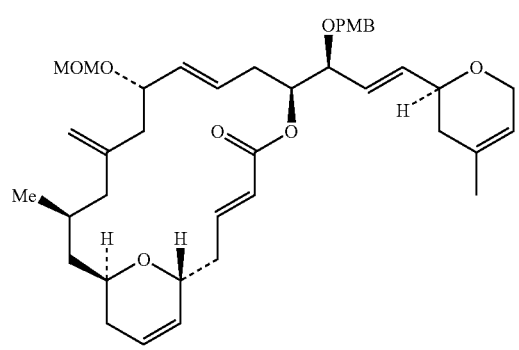
(36)

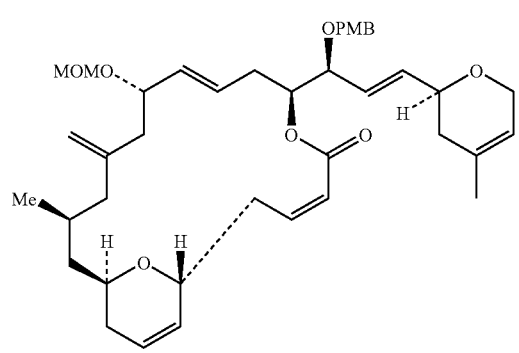
(37)

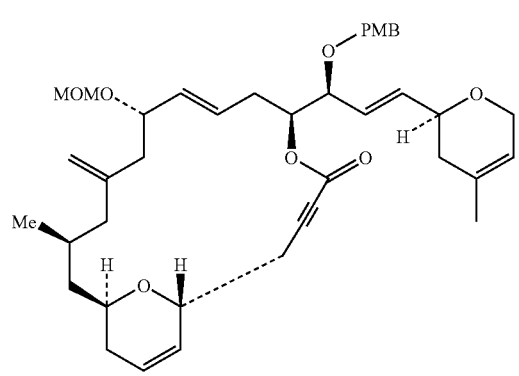
(39)

Desoxy-deoxylaulimalide (13) and deoxylaulimalide (53) also have been prepared. In these preparations, opening of epoxide (50) with lithiated methyl benzothiazolyl sulphone in the presence of hexamethylphosphoramide (HMPA) provided the corresponding alcohol, which then was reacted with 2.2 equiv of potassium hexamethyldisilazane (KHMDS) in ethylene glycol dimethyl ether (DME) (Scheme 9). The resulting dianion was reacted with the aldehyde derived from a Swern oxidation of alcohol (31) to provide a mixture (4:1) of E- and Z-olefins in 64% yield. After chromatographic separation, E-olefin (51) was treated with camphor sulfonic acid (CSA) in methanol to provide the corresponding diol, which was converted to the corresponding epoxide by selective mesylation followed by treatment of the primary mesylate with potassium carbonate in methanol (MeOH) in a one pot, two-step sequence. Opening of the resulting epoxide with lithiated methyl phenylsulphone in the presence of HMPA at −78° C. provided desired sulfone derivative (52). Sulfone (52) was converted to compounds (13) and (53) by employing a Julia olefination with fragment (15) and macrolactonization of the corresponding hydroxy alkynoic acid.

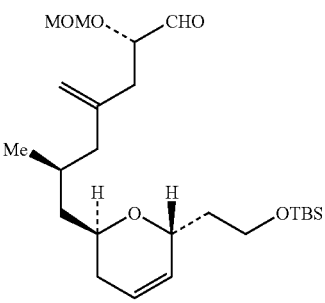
(15)

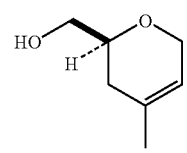
(31)

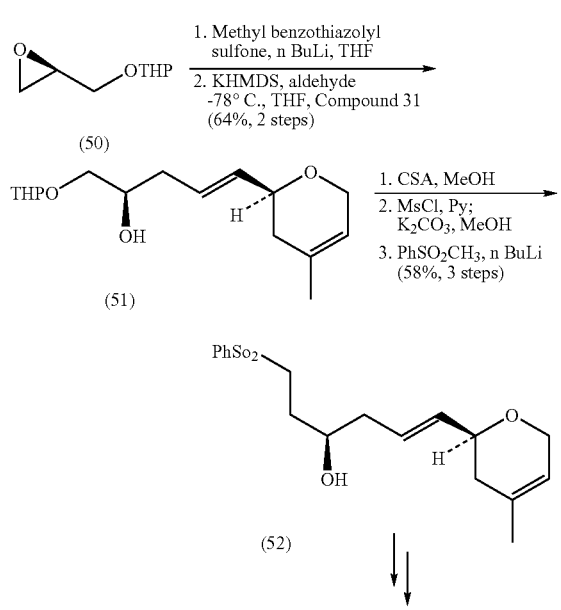

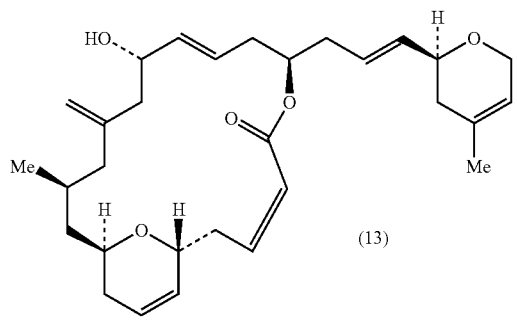
(13)

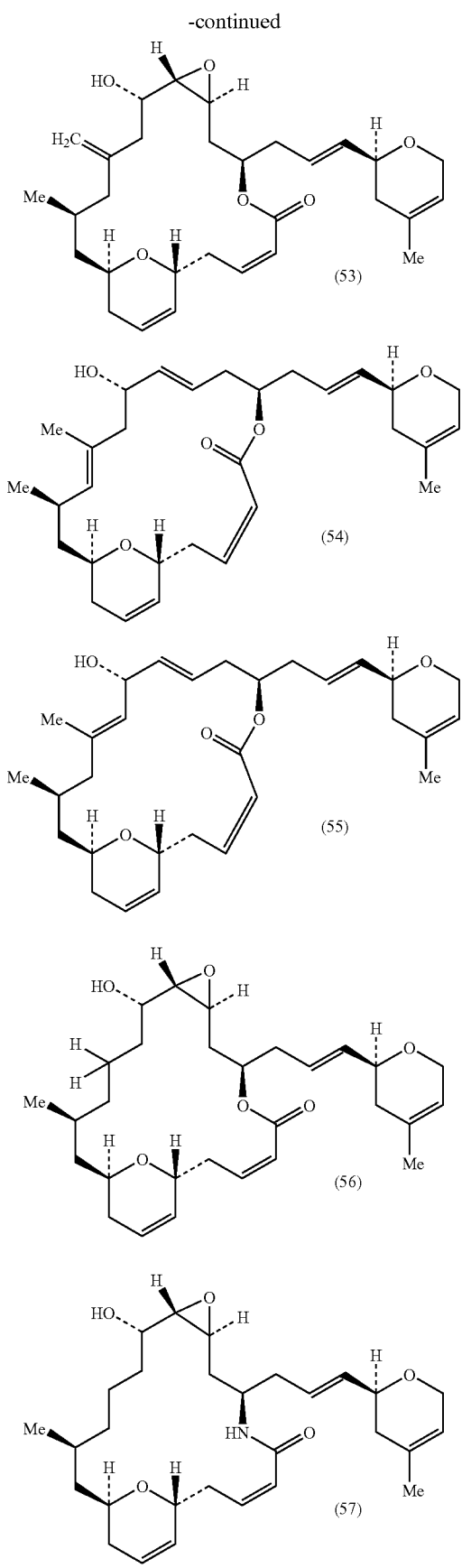

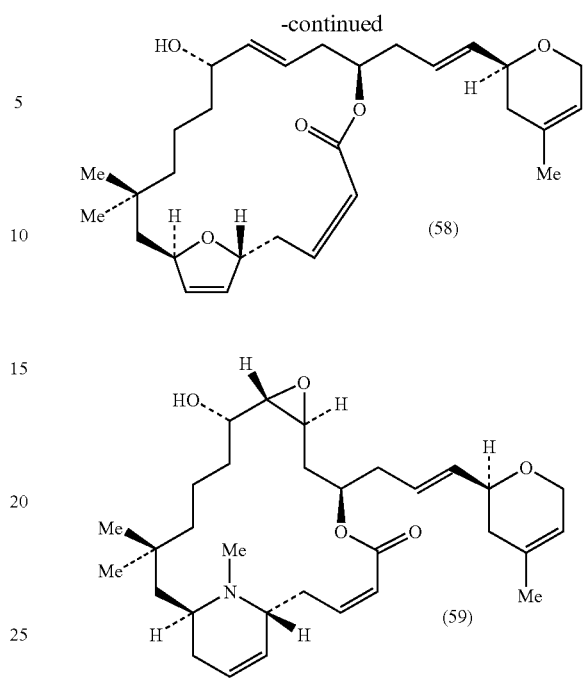

Preparation of deoxy-desoxylaulimalide (compound 13) is outlined in Scheme 9. The methyl ether analog of the $C_{20}$-hydroxyl group can be prepared by removal of the PMB-ether in compound (37) and etherification under standard conditions. Removal and isomerization of the $C_{15}$-hydroxyl stereochemistry can be carried out by standard synthetic manipulation of compound (27) (Scheme 10). Barton deoxygenation (D. H. R. Barton et al., *Chem. Soc. Perkins Trans.*, 1, 1514–1585 (1975)) of the hydroxyl group of compound (27) provides corresponding precursor compound (60). Mitsunobu inversion (S. F. Martin et al., *Tetrahedron Lett.*, 32, 3017–20 (1991); *Synthesis*, 1–28 (1981) and D. Evans, *J. Chem. Soc. (A)*, 3133–3142 (1968)) of alcohol (27) with triphenylphosphine ($Ph_3P$) and p-nitrobenzoic acid in the presence of diethylazodicarboxylate followed by aqueous lithium hydroxide promoted saponification of the resulting benzoate derivative to furnish compound (61) that can be converted to compound (62) using standard synthetic manipulation. Julia coupling of compound (62) with fragment (16) followed by macrocyclization as described for laulimalide provide a convenient access to the corresponding compounds.

For isomerization of the $C_{13}$-olefin, as represented in compounds (54) and (55), rhodium-catalyzed olefin isomerization of compound (27) was used. The dihydropyran double bond also can isomerize under these conditions. In that case, the importance of the $C_6$–$C_7$ double bond (for laulimalide) can be determined. The $C_{13}$–$C_{14}$ olefin in compound (55) can be accessed from iodide 24. Alkyne derivative (63) can be prepared from the corresponding known alkyne derivative (W. Oppolzer et al., *Tetrahedron Lett.*, 31, 6995–6998 (1990)) by standard protecting group manipulation. Negishi coupling (E. Negishi et al., *J. Am. Chem. Soc.*, 100, 2254–2256 (1978)) of vinyl iodide (64) with iodide (24) furnishes the alkene derivative (65) that can be converted to compound (55) as described for laulimalide.

Scheme 10

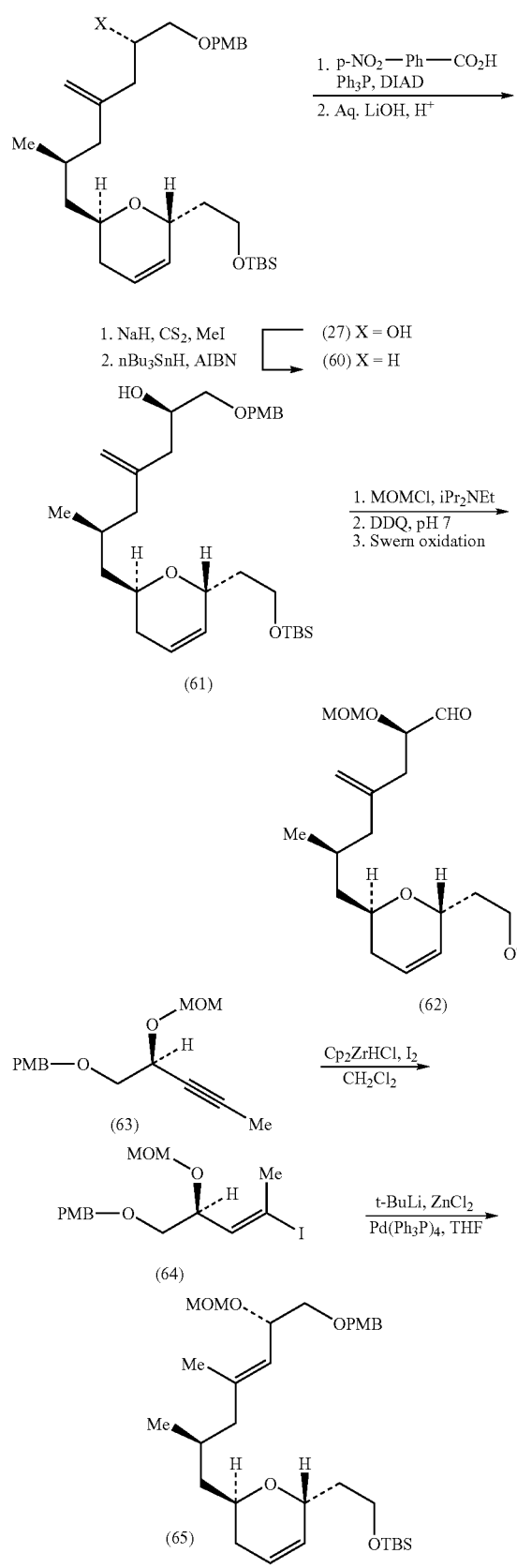

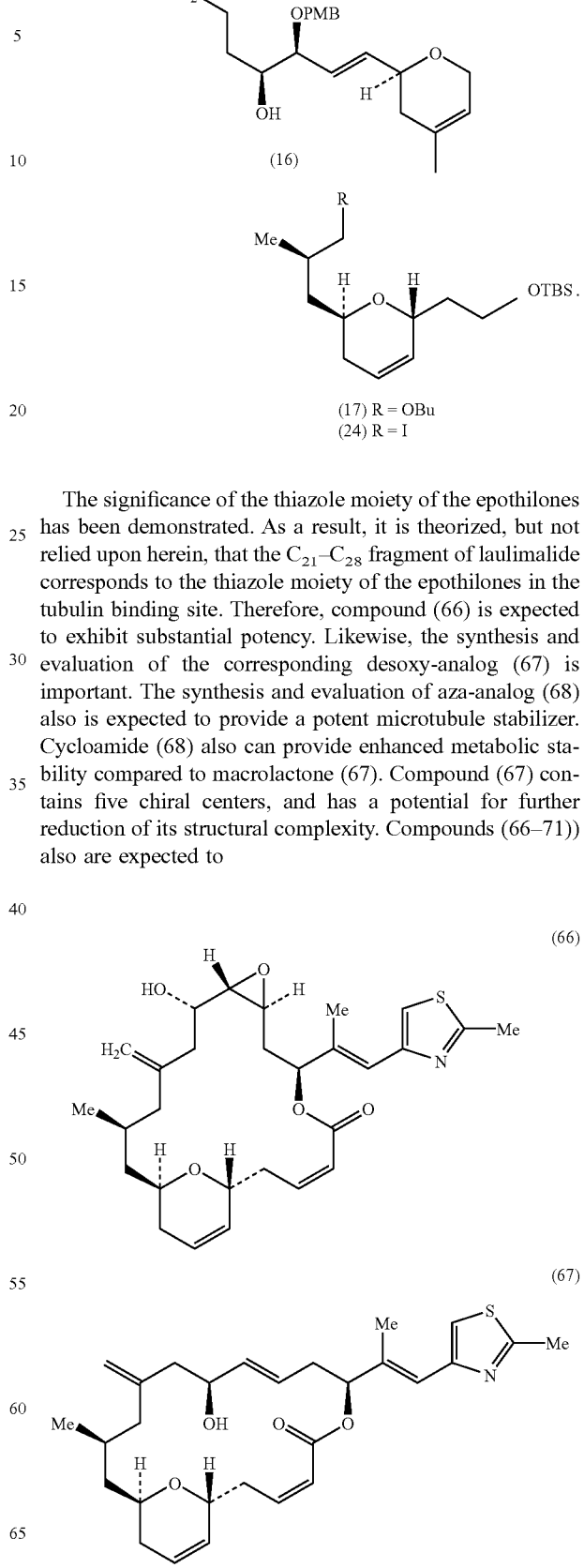

The significance of the thiazole moiety of the epothilones has been demonstrated. As a result, it is theorized, but not relied upon herein, that the $C_{21}$–$C_{28}$ fragment of laulimalide corresponds to the thiazole moiety of the epothilones in the tubulin binding site. Therefore, compound (66) is expected to exhibit substantial potency. Likewise, the synthesis and evaluation of the corresponding desoxy-analog (67) is important. The synthesis and evaluation of aza-analog (68) also is expected to provide a potent microtubule stabilizer. Cycloamide (68) also can provide enhanced metabolic stability compared to macrolactone (67). Compound (67) contains five chiral centers, and has a potential for further reduction of its structural complexity. Compounds (66–71)) also are expected to -continued

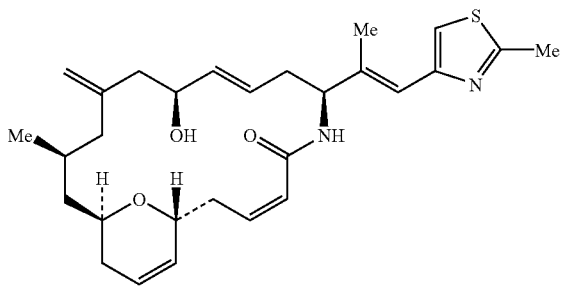

(68)

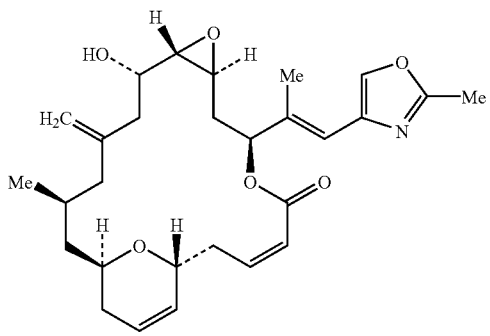

(69)

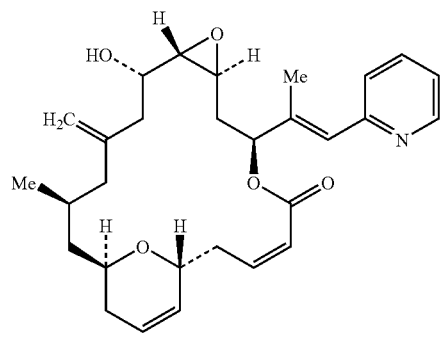

(70)

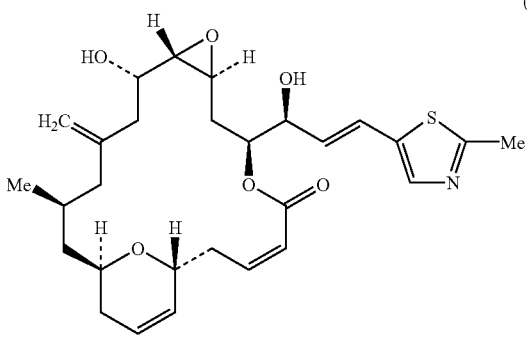

(71)

demonstrate tublin binding properties. In particular, compounds (69–71) were designed based upon studies that indicated an effective replacement of the thiazole with other heteroaryl groups.

For the synthesis of other thiazole-containing compounds of the present invention, a thiazole template for Julia coupling is prepared as outlined in Scheme 11. Additional compounds of the present invention can be prepared by substituting other heteroaryl aldehyde for compound (72).

Wittig olefination of known aldehyde (72) (K. C. Nicolaou, *J. Am. Chem. Soc.*, 119, 7960–7973 (1997)) with 2-(triphenylphosphoranylidene)propionaldehyde in benzene at reflux provides the α,β-unsaturated aldehyde (73). Corey-Chakovsky epoxidation (E. J. Corey et al., *J. Am. Chem. Soc.*, 87, 1353–1364 (1965)) of aldehyde (73) provides racemic epoxide (74). In the event that the sulfur ylid epoxidation provides a cyclopropane rather than an epoxide, the desired epoxidation can be prepared by alternative procedures (e.g., M. L. Vazquez et al., *J. Med. Chem.*, 38, 581–584 (1995)). Opening of epoxide (74) with lithiated methyl phenylsulfone in the presence of HMPA at −78° C. provides racemic alcohol (75). The racemic synthesis, as opposed to the enantioselective synthesis, provides rapid access to both enantiomers for the synthesis of compounds (66) and (67), as well as aza-analog (68). The racemic mixture can be resolved by formation of a diastereomeric mixture with an optically active acid, such as mandelic acid, or by an enzymatic acylation protocol using lipase PS-30, for example. The absolute stereochemistry of the resolved alcohol can be determined by NMR analysis of the corresponding Mosher ester (J. A. Dale et al., *J. Org. Chem.*, 34, 2543–2549 (1969)). Sulfone derivative (76) can be used in the Julia olefination with aldehyde (15) as described for the synthesis of laulimalide to provide access to compounds (66) and (67).

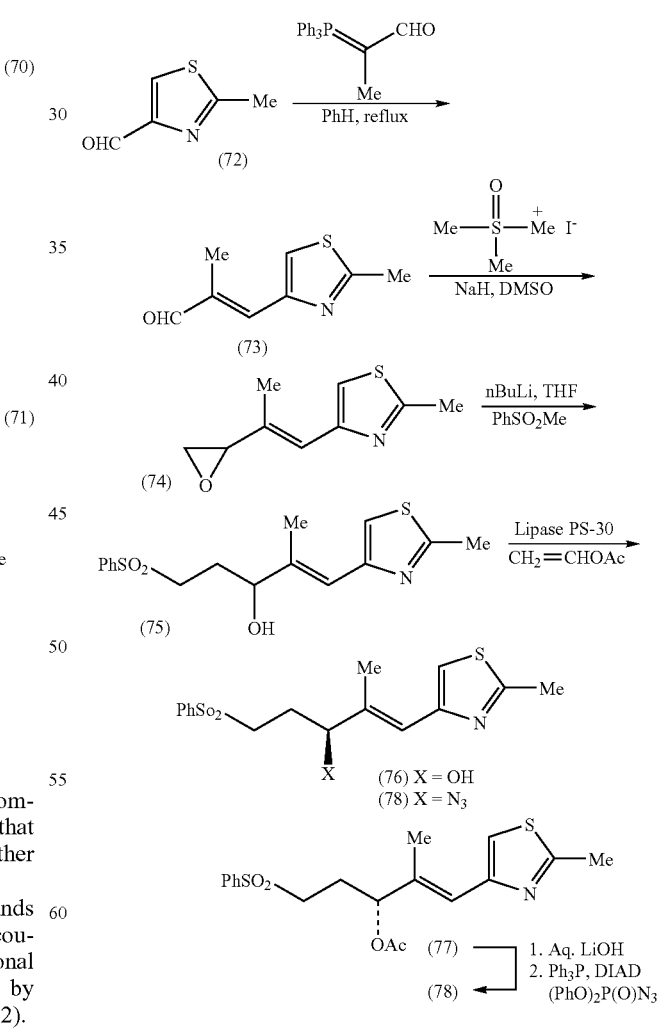

Utilizing appropriate and available aldehydes, the preparation of compounds (69) and (70) can be achieved using analogous procedures.

The epimeric alcohol derived from compound (77) can be utilized in the synthesis of cycloamide derivative (68). Ester hydrolysis of compound (77), followed by Mitsunobu azidation of the resulting alcohol, provides azide derivative (78). Julia olefination of sulfone (78) and aldehyde (15) followed by Yamaguchi cycloamidation of the corresponding amine provides compound (68) after standard synthetic manipulation. For the synthesis of compound (71), aldehyde (72) can be reacted with sulfone derivative (42) to provide the corresponding olefin. Olefin isomerization followed by sulfone formation generally as described for compound (52) provides the desired template for Julia reaction with aldehyde (15).

(42)

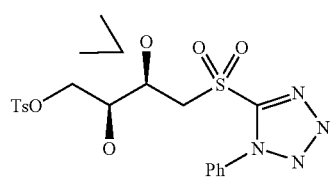

The $C_{15}$-hydroxyl group of laulimalide corresponds to the $C_3$-hydroxyl group of epothilone in the tubulin binding site. Therefore, it is theorized that the $C_2$–$C_3$ cis-olefin functionality can be removed, and the $C_{15}$-hydroxyl group of laulimalide can be translocated to the $C_3$-position, as in compound (79), which has excellent pharmacophore matching with the epothilone bioactive model. Corresponding desoxy derivatives (80) and (81) also are prepared. Compounds (83) ($R^5$=H) and (84) ($R^5$=H) also are prepared and compared for biological properties to compounds (81) and (82). Compounds (85) and (86) have been designed to replace the $C_{21}$–$C_{28}$ segment with thiazole derivatives. Compound (86), having a cycloamide functionality, is expected to be a potent microtubule stabilizing agent having as few as four chiral centers.

(79)

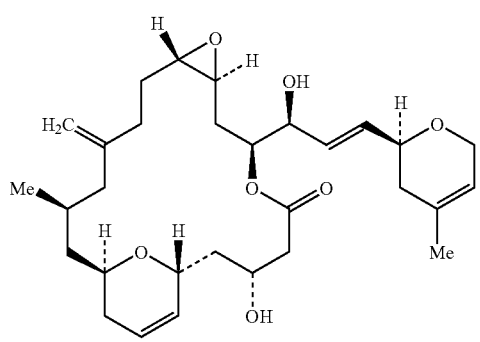

(80)

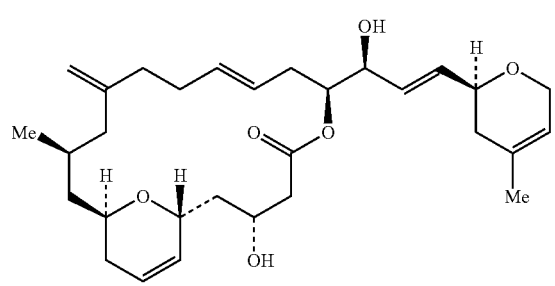

-continued (81)

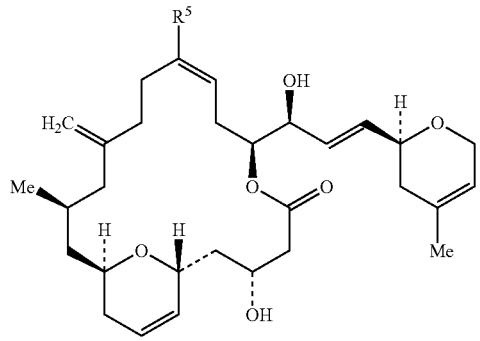

(82) p = 1, q = 1
(83) p = 0, q = 1
(84) p = 0, q = 0

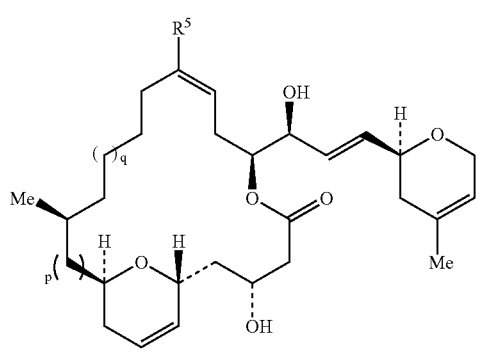

(85)

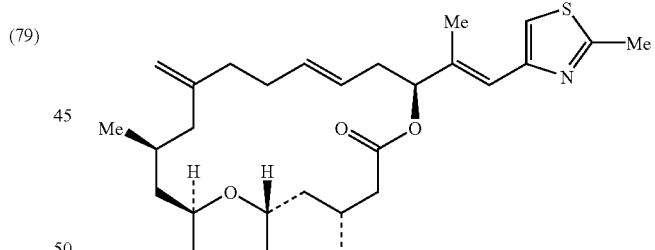

(86)

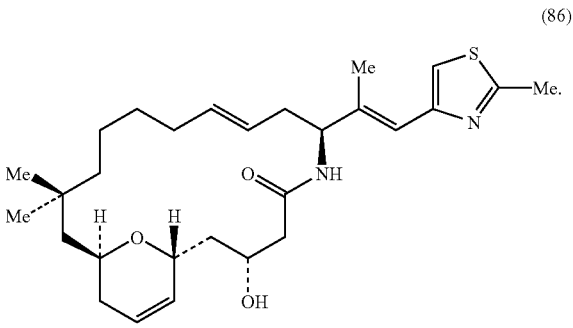

The synthesis of $C_3$-hydroxyl derivative (79) can be carried out from known intermediate (14). Aldehyde (87) can be prepared from compound (14) by Sharpless asymmetric epoxidation and dehydroxylation reactions as the key steps. Acetate aldol reaction of compound (87) with the enolate of ethyl acetate followed by protection of the $C_3$-hydroxyl group as a TBS-ether (tert-butyldimethyl-silyl-ether) provides compound (88) as a mixture of diastereomers at the $C_3$-position. Removal of the tetrahydropyran (THP) ether and ester hydrolysis followed by macrolactonization of the resulting hydroxy acid using Yamaguchi protocol furnishes a mixture of macrolactones (89) and (90). The mixture of diastereomers can be separated at this stage. Removal of the TBS- and PMB-ethers of compounds (89) and (90) provides $C_3$-hydroxyl compound (79) and its $C_3$-epimer for biological evaluation. Depending upon the tubulin binding properties of compounds (79) and epi-(79), either diastereomer can be prepared by asymmetric acetate aldol reaction of the Z-(O)-boron enolate derived from optically active acetylbornane-10,2-sultam (J. D. Brabender et al., *Synlett.*, 824–825 (1997)).

The synthesis of desoxy derivative (80) can be carried out from

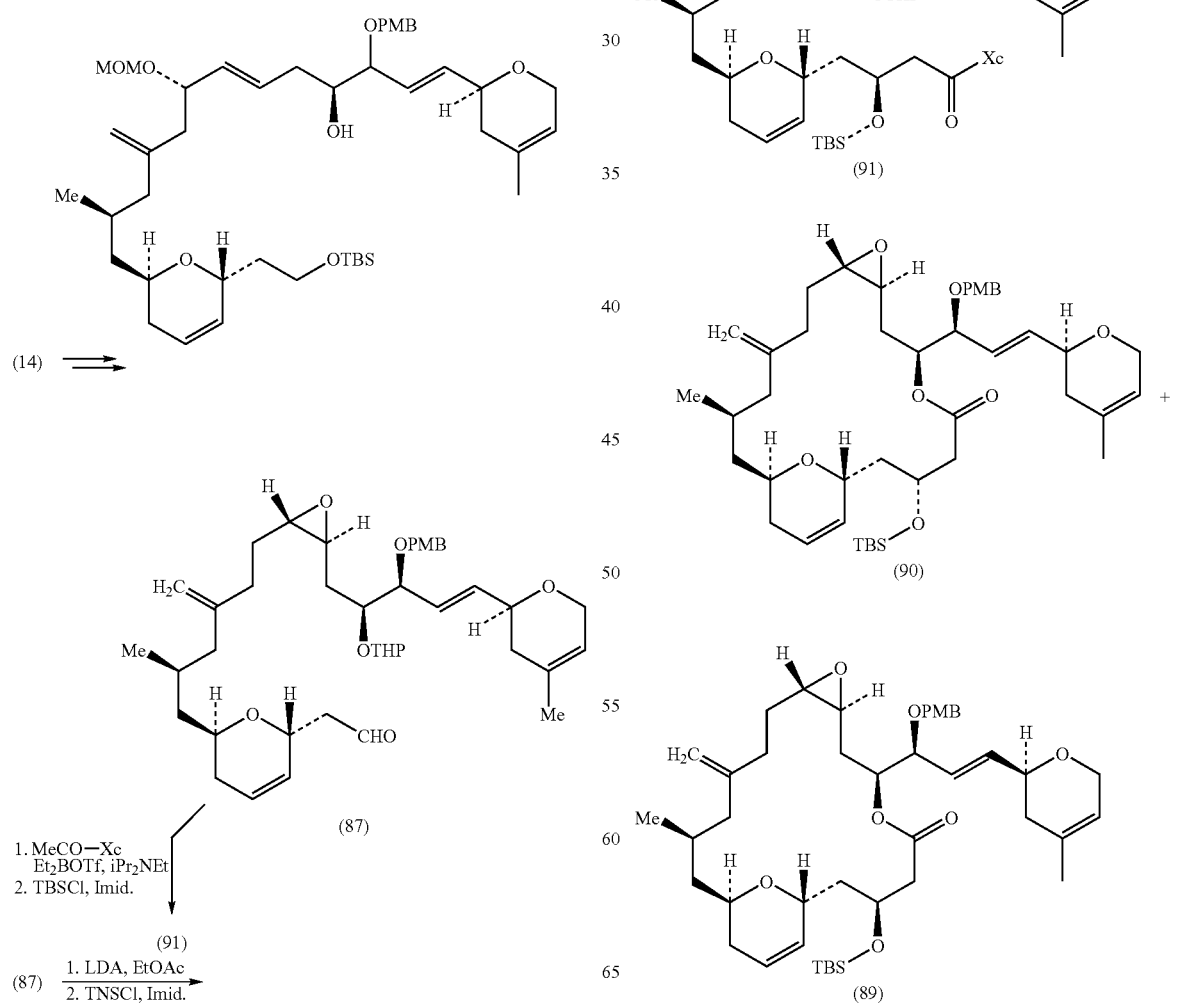

-continued

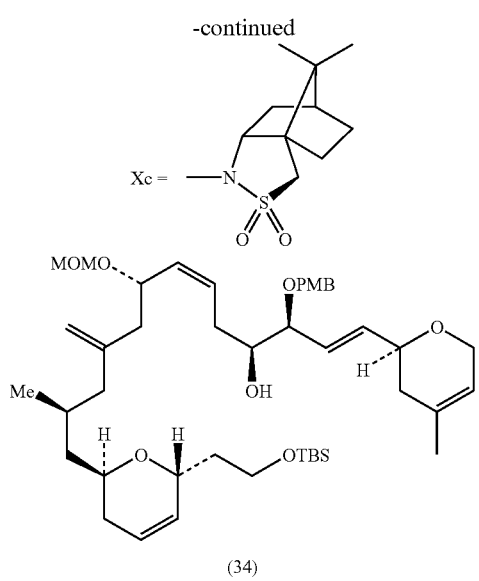

(34)

intermediate (60) by following analogous procedures. Various compounds containing $C_{16}$–$C_{17}$ cis-olefin geometry are prepared from compound (34) which was obtained as a minor isomer during Julia olefination of aldehyde (15) and sulfone derivative (16). When the γ-hydroxyl group of compound (16) was protected as a TIPS-ether (triisopropylsilyl-ether), the corresponding Julia olefination with compound (15) provided a 1:1 mixture of cis/trans isomers in 45–50% isolated yield. These derivatives were prepared for initial biological evaluation from the cis-isomer derived from the Julia reaction.

(Compound 12a)

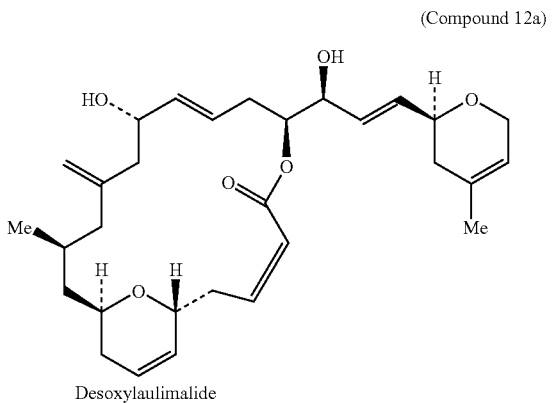

Desoxylaulimalide

The synthesis of desoxylaulimalide (12a) was carried out from the known precursor (200) as described in A. K. Ghosh et al., *J. Org. Chem.*, 66, 8973–82 (2001) and A. K. Ghosh et al., *Am. Chem. Soc.*, 122, 11027–11029 (2000). Protection of the alcohol as a MOM ether with chloromethyl methyl ether (MOMCl) and diisopropylethylamine ($iPr_2EtN$) in $CH_2Cl_2$ followed by removal of the TBS group by treatment with tetrabutylammonium fluoride ($nBu_4N^+F^-$) in tetrahydrofuran (THF) provided primary alcohol (201) (Scheme 1). Dess-Martin oxidation of (201) (S. D. Meger et al., *Org. Chem.*, 59, 7549–7752 (1994)) provided the aldehyde which was subjected to Corey et al. homologation conditions (E. J. Corey, *Tetrahedron Lett.*, 13, 3769–3773 (1972)) using carbon tetrabromide ($CBr_4$) and $PPh_3$ in $CH_2Cl_2$ to provide the corresponding dibromo olfefin. Treatment of the resulting dibromo olefin with n-butyl lithium (nBuLi) at −78° C. provided the alkynyl anion, which upon treatment with methyl chloroformate furnished alkynyl ester (202). Removal of the PMB ether by exposure to 2,3-dichloro-5,6-dicyano-1,4-benzoquinone (DDQ), followed by saponification of the methyl ester by exposure to aqueous lithium hydroxide, provided the corresponding precursor hydroxy acid. Yamaguchi macrolactonization (J. Inanaga et al., *Bull. Chem. Soc. Jpn.*, 53, 1989–1993 (1979)) of the resulting hydroxy acid afforded lactone (203). Hydrogenation of lactone (203) over Lindlar's catalyst in a mixture (1:1) of 1-hexene and EtOAc followed by removal of the MOM protecting groups by exposure to $Me_2BBr$ in $CH_2Cl_2$ (Y. Guindon et al., *Tetrahedron Lett.*, 24, 3969–3973 (1983)) yielded desoxylaulimalide (12).

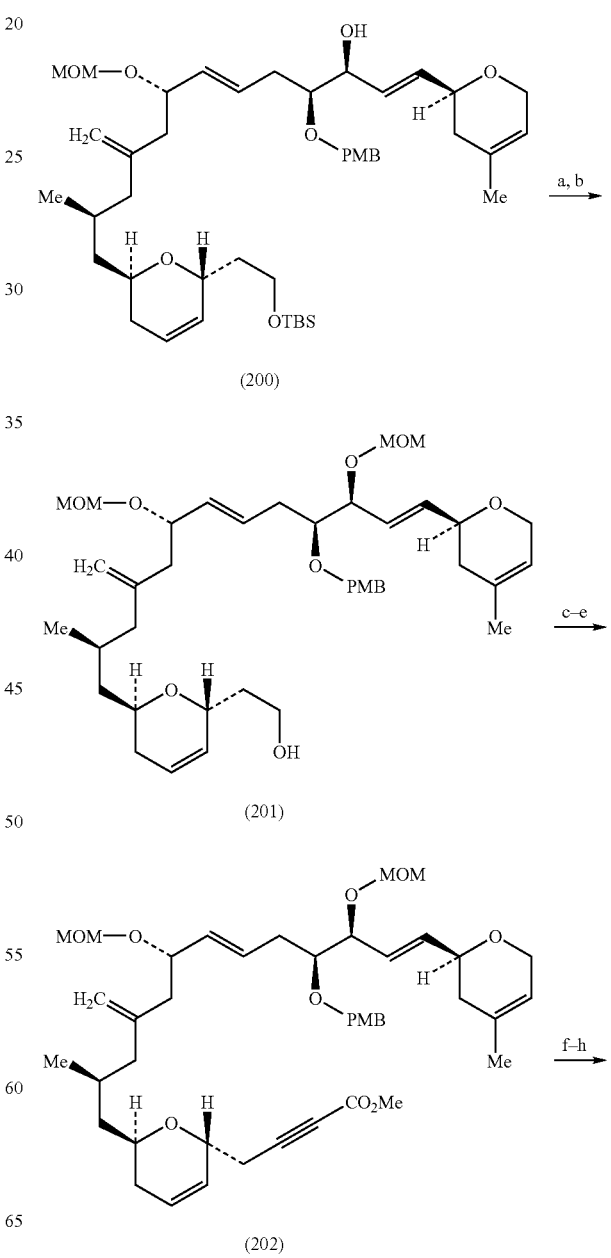

-continued

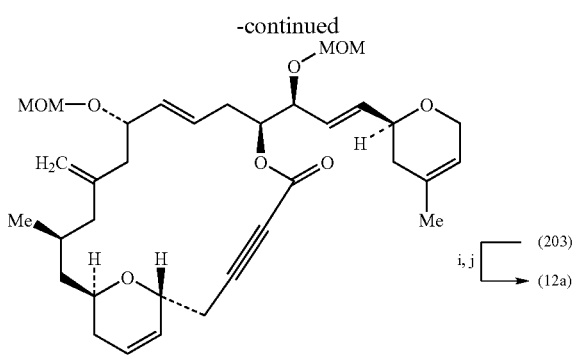

(a) MeOCH₂Cl, iPr₂Et, CH₂Cl₂; (b) TBAF, THF (86% for 2 steps); (c) Dess-Martin, CH₂Cl₂; (d) CBr₄, PPh₃, CH₂Cl₂, 0° C.; (e) nBuLi, THF, −78° C., then ClCO₂Me, −78° C. (45% for 3 steps); (f) DDQ, CH₂Cl₂, pH 7 buffer; (g) LiOH, THF, H₂O; (h) Cl₃PhCOCl, iPr₂NEt, THF, then DMAP, benzene (54% for 3 steps); (i) H₂, Lindlar's catalyst, 1-hexene, EtOAc; (j) Me₂BBr, CH₂Cl₂ (75% for 2 steps)

Preparation of MOM Derivative (201):

To a stirred solution of alcohol (200) (109 mg, 0.145 mmol) in methylene chloride (CH₂Cl₂) (5 mL) was added iPr₂NEt (380 μL) followed by MOMCl (110 μL). After stirring at 23° C. for 24 hours, the mixture was washed with aqueous 1 M sodium bisulfate (NaHSO₄), brine, dried over anhydrous sodium sulfate (Na₂SO₄) and evaporated. The residue was dissolved in THF, then (nBu₄N⁺F⁻) (0.5 mL, 1.0 M in THF) was added dropwise. The resulting mixture was stirred at 23° C. for 2 hours. The mixture was quenched with saturated aqueous ammonium chloride (NH₄Cl) and extracted with ethyl acetate (EtOAc). The combined organic layers were washed with brine, dried over Na₂SO₄, and concentrated under reduced pressure. The residue was purified by silica gel chromatography (50% EtOAc/hexane) to afford compound (201) as a colorless oil (124 mg, 86% for 2 steps).

Preparation of Alkynyl Ester (202):

To a stirred solution of alcohol (201) (124 mg) in wet CH₂Cl₂ (2 mL) was added Dess-Martin periodinane (106 mg). The resulting white suspension was stirred for 30 minutes. The mixture then was subjected to direct silica gel chromatography eluting with 20% EtOAc/hexane to afford the corresponding aldehyde as a colorless oil, which was used for next reaction immediately. To a stirred solution of carbon tetrabromide (CBr₄) (66 mg) in CH₂Cl₂ (3 mL) at 0° C. was sequentially added PPh₃ (105 mg) and triethylamine (Et₃N) (56 mg). The resulting yellow solution was-stirred for 30 minutes. A solution of the above aldehyde in CH₂Cl₂ (3 mL) was added dropwise. The mixture was stirred at 0° C. for 30 minutes. After this period, the mixture was washed with saturated aqueous sodium-bicarbonate (NaHCO₃), 1 M NaHSO₄, and brine. The organic layer was dried over anhydrous Na₂SO₄ and concentrated. The residue was filtered through CELITE™ to provide the dibromide, which was used immediately in the next reaction. To a stirred solution of the above dibromide (27 mg) in THF (1.5 mL) at −78° C. was added nBuLi (88 μL, 1.6 M in hexane) dropwise. The resulting red mixture was stirred for 10 minutes. Methyl chloroformate (ClCO₂Me) (100 μL) was added dropwise. The mixture was stirred at −78° C. for 30 minutes, then quenched by saturated aqueous NH₄Cl. The mixture was extracted with EtOAc. The organic layer was washed with brine, dried over Na₂SO₄, and concentrated. The residue was purified by silica gel chromatography (20% EtOAc/hexane) to afford alkynyl ester (202) (16 mg, 43% yield for three steps).

Macrolactone (203):

To a solution of the above PMB ether (10 mg) in CH₂Cl₂ (1 mL) was added pH 7 buffer (0.1 mL) followed by DDQ (11 mg). The resulting mixture was stirred at 23° C. for 1 hour, then quenched with saturated aqueous NaHCO₃. The layers were separated, and the aqueous layer was extracted with CH₂Cl₂. The combined organic layers were dried over anhydrous Na₂SO₄ and concentrated. The residue was purified by silica gel chromatography (40% EtOAc/hexane) to give the alcohol as a colorless oil. The alcohol was dissolved in THF (1 mL). A solution of lithium hydroxide (LiOH) (8 mg) in water (0.5 mL) was added. The resulting mixture was stirred for 1.5 hours, then saturated aqueous NH₄Cl was added. The mixture was acidified to pH 4 with 1N hydrochloric acid (HCl) at 0° C., then extracted with EtOAc. The organic layer was washed with brine, dried over Na₂SO₄, and concentrated to provide the acid. To a stirred solution of the above hydroxy acid in THF (5 mL) was added iPr₂NEt (316 μL, 0.16 M in benzene) and trichlorobenzoyl chloride (265 μL, 0.13 M in benzene). The resulting mixture was stirred for 30 minutes, then concentrated under reduced pressure. The residue was dissolved in benzene (60 mL). 4-Dimethylaminopyridine (DMAP) (8 mg) in benzene (5 mL) was added dropwise to the resulting solution over a period of 30 minutes. The resulting suspension was stirred for 12 hours, then the mixture was diluted with EtOAc and washed with saturated aqueous NaHCO₃ and aqueous 1 M NaHSO₄. The aqueous layer was extracted with EtOAc. The combined organic layers were washed with brine, dried over Na₂SO₄, and concentrated. The residue was purified by silica gel chromatography (30% EtOAc/hexane) to provide lactone (203) as a colorless oil (5 mg, 54%).

Preparation of Desoxylaulimalide (12a):

To a solution of lactone (203) (5 mg) in 1-hexene (1 mL) and EtOAc (1 mL) was added Lindlar's catalyst (2 mg). The resulting suspension was vigorously stirred under a hydrogen balloon for 1 hour. The mixture then was filtered through a pad of CELITE™ and the filter pad was washed with EtOAc. Concentration of the filtrate gave a residue that was purified by silica gel chromatography (30% EtOAc/hexane) to afford the corresponding MOM protected cis-macrolactone (4 mg).

Dimethylboron bromide (Me₂BBr) (300 μL, 0.1 M in CH₂Cl₂) was added to a stirred solution of above macrolacetone in CH₂Cl₂ (1 mL) at −78° C. The resulting mixture was stirred for at −78° C. for 30 minutes. The reaction was quenched at −78° C. by the addition of a mixture of THF and saturated NaHCO₃ solution. The mixture was warmed to 23° C., then extracted with EtOAc. The organic layer was washed with brine, dried over anhydrous Na₂SO₄, and evaporated. The residue was chromatographed over silica gel eluting with 50% EtOAc/hexane to yield desoxylaulimalide (12a) (0.8 mg). ¹H-NMR (400 MHz, CDCl₃) δ: 7.22 (d, J=8.6 Hz, 2H), 6.86 (d, J=8.6 Hz, 2H), 6.31 (m, 1H), 5.91(d, J=11.6 Hz, 1H), 5.84 (dd, J=15.6, 6.2 Hz, 1H), 5.83 (m, 1H), 5.70 (d, J=10.6 Hz, 1H), 5.63–5.58 (m, 3H), 5.43 (s, 1H), 5.06 (m, 1H), 4.84 (s, 2H), 4.59 (d, J=11.8 Hz, 1H), 4.31 (d, J=11.8 Hz, 1H), 4.19 (s, 2H), 4.15–4.06 (m, 3H), 3.85 (m, 1H), 3.80 (s, 3H), 3.55 (m, 1H), 2.33–1.76 (m, 12H), 1.71 (s, 3H), 1.65 (m, 1H), 1.37–1.12 (m, 3H), 0.79 (d, J=6.8 Hz, 3H).

The cytotoxic activity of trans-desoxylaulimalide (12a) was evaluated. An initial cytotoxicity study with desoxylaulimalide (12a) was conducted to compare compound (12a) to taxol and laulimalide for effects on the growth of human MCF-7 breast cancer cells. Cytotoxicity assays on MCF-7 were performed as described in P. Giannakakou et al., *J. Biol. Chem.*, 272, 17118–17125 (1997). Consistent with its activity in a tubulin assembly assay, desoxylaulimalide (12a) was an inhibitor of cell growth. In particular, $IC_{50}$ values of 360, 7.0, and 2.4 nM were obtained for desoxylaulimalide (12a), laulimalide (2), and taxol (1), respectively. Thus, desoxylaulimalide (12a) is about 1/50 as active as laulimalide in the MCF-7 cells. This compares with the 340-fold lower activity in MDA-MB-435 breast cancer cells observed for isolaulimalide (9), which also lacks the epoxide moiety.

(9)

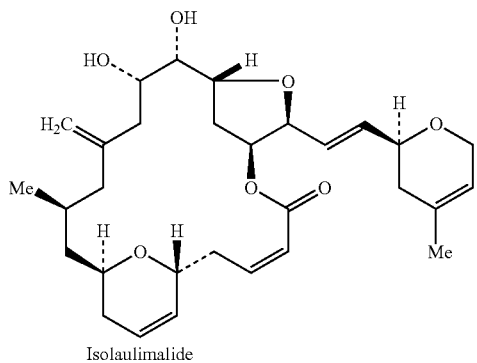

Isolaulimalide

Although less active than laulimalide, desoxylaulimalide (12a) stimulates the tubulin assembly reaction and inhibits the growth of MCF-7 cells. The activity of desoxylaulimalide (12a) occurred even through the $C_{16}$–$C_{17}$ olefin bond is in the trans-configuration, while configuration of the macrocycle at the $C_{16}$–$C_{17}$ epoxide in laulimalide is in the cis-configuration.

Obviously, many modifications and variations of the invention as hereinbefore set forth can be made without departing from the spirit and scope thereof, and, therefore, only such limitations should be imposed as are indicated by the appended claims.

What is claimed is:

1. A method of treating an individual suffering from a cancer wherein stabilization of microtubules provides a benefit, comprising administration of therapeutically effective amount of a compound to the individual, wherein the cancer is a breast cancer, an ovarian cancer, a lung cancer, a myeloid leukemia, or a skin cancer, and wherein the compound has a general formula

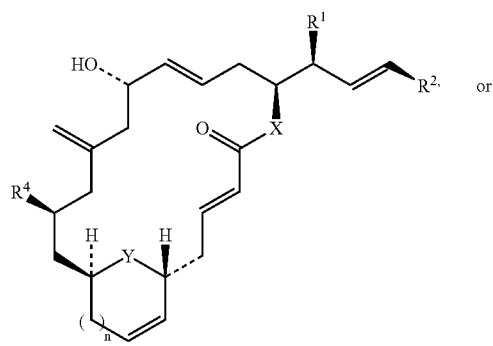

-continued

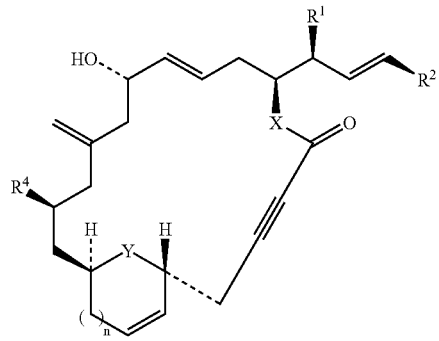

wherein $R^1$ is selected from the group consisting of hydro, $OR^a$, and $C_{1-3}$alkyl;

$R^2$ is selected from the group consisting of a saturated or unsaturated monocyclic 3–7 membered heterocyclic ring having 1–3 heteroatoms selected from the group consisting of oxygen, nitrogen, and sulfur, $C_{3-7}$cycloalkyl, $C_{3-7}$cycloalkenyl, and a monocyclic or bicyclic ring system containing five to ten atoms and one or two aromatic rings and containing one to four heteroatoms selected from nitrogen, oxygen, and sulfur in the aromatic ring;

$R^4$ is $C_{1-4}$alkyl;

X and Y, independently, are selected from the group consisting of O and $NR^a$;

$R^a$ is selected from the group consisting of hydro and $C_{1-4}$alkyl;

n is 0 or 1;

or a pharmaceutically acceptable salt thereof.

2. The method of claim 1 wherein $R^1$ is H, $OR^a$, or $CH_3$; $R^2$ is an unsaturated monocyclic five or six membered heterocyclic ring having 1 to 3 heteroatoms selected from the group consisting of oxygen, nitrogen, and sulfur or a monocyclic or bicyclic ring system containing five to ten atoms and one or two aromatic rings and containing one to four heteroatoms selected from nitrogen, oxygen, and sulfur in the aromatic ring.

3. The method of claim 1 wherein $R^1$ is H or OH; $R^2$ is an unsaturated monocyclic five or six membered heterocyclic ring having one oxygen atom, or a monocyclic or bicyclic ring system containing five to ten atoms and one or two aromatic rings and containing one to four heteroatoms selected from nitrogen, oxygen, and sulfur in the aromatic ring; $R^4$ is $CH_3$; $R^a$ is H or $CH_3$; and n is 1.

4. The method of claim 3 wherein $R^2$ is substituted with a $C_{1-3}$alkyl group.

5. The method of claim 1 wherein $R^1$ is H or OH; $R^2$ is

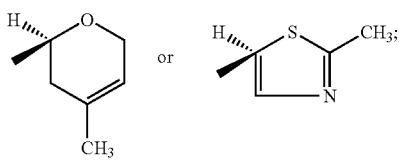

$R^4$ is $CH_3$; X is O or NH; Y is O or N—$CH_3$; and n is 1.

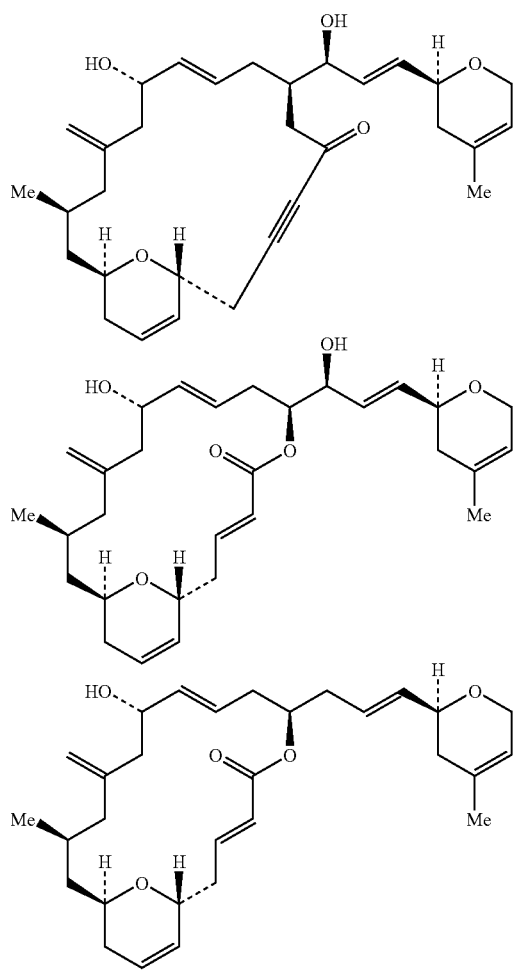
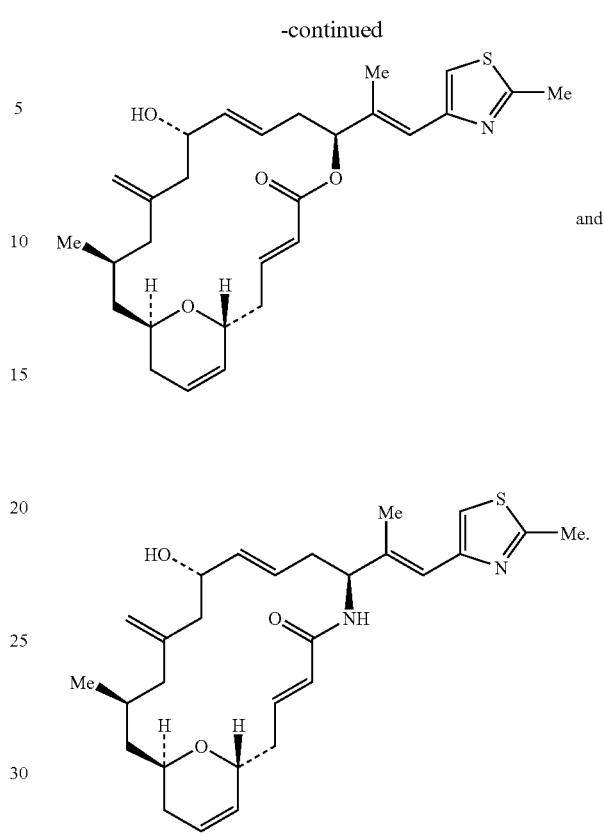
-continued
6. The method of claim 1 wherein the compound has a structural formula.